(12) United States Patent
Fahrenbach et al.

(10) Patent No.: US 9,120,799 B2
(45) Date of Patent: Sep. 1, 2015

(54) CRYSTALLINE BIPYRIDINIUM RADICAL COMPLEXES AND USES THEREOF

(71) Applicant: NORTHWESTERN UNIVERSITY, Evanston, IL (US)

(72) Inventors: Albert C. Fahrenbach, Lebanon, IN (US); Jonathan C. Barnes, Evanston, IL (US); Hao Li, Austin, TX (US); J. Fraser Stoddart, Evanston, IL (US); Ashish Neil Basuray, Chicago, IL (US); Srinivasan Sampath, Daejeon (KR)

(73) Assignee: NORTHWESTERN UNIVERSITY, Evanston, IL (US)

( * ) Notice: Subject to any disclaimer, the term of this patent is extended or adjusted under 35 U.S.C. 154(b) by 182 days.

(21) Appl. No.: 13/623,935

(22) Filed: Sep. 21, 2012

(65) Prior Publication Data

US 2015/0191470 A1 Jul. 9, 2015

Related U.S. Application Data

(60) Provisional application No. 61/537,852, filed on Sep. 22, 2011.

(51) Int. Cl.
| | | |
|---|---|---|
| *H01M 4/60* | (2006.01) | |
| *C07F 15/00* | (2006.01) | |
| *C07D 213/89* | (2006.01) | |
| *C07D 471/22* | (2006.01) | |
| *C30B 7/00* | (2006.01) | |
| *C30B 30/04* | (2006.01) | |
| *C30B 29/54* | (2006.01) | |
| *C30B 29/62* | (2006.01) | |
| *H01M 4/00* | (2006.01) | |

(52) U.S. Cl.
CPC .......... *C07D 471/22* (2013.01); *C07F 15/0046* (2013.01); *C07F 15/0053* (2013.01); *C30B 7/00* (2013.01); *C30B 29/54* (2013.01); *C30B 29/62* (2013.01); *C30B 30/04* (2013.01); *C07D 213/89* (2013.01); *H01M 4/00* (2013.01)

(58) Field of Classification Search
CPC ............ C07F 15/0046; C07F 15/0053; C07D 213/89; H01M 4/60
USPC ........... 429/213; 436/164; 136/263, 256, 258; 252/500
See application file for complete search history.

(56) References Cited

U.S. PATENT DOCUMENTS

| | | | | |
|---|---|---|---|---|
| 5,531,871 | A * | 7/1996 | Fauteux et al. | 205/688 |
| 5,538,655 | A * | 7/1996 | Fauteux et al. | 252/62.2 |
| 6,130,096 | A * | 10/2000 | Tinker et al. | 436/164 |
| 6,855,950 | B2 * | 2/2005 | McCreery | 257/40 |
| 6,995,312 | B2 * | 2/2006 | Zhou et al. | 136/263 |

FOREIGN PATENT DOCUMENTS

WO WO 2009149381 A2 * 12/2009 ................ C07F 3/00

OTHER PUBLICATIONS

Ali Trabolsi et al., "A tristable [2]pseudo[2]rotaxane", Chem. Commun., 2010, 46, 871-873. Published Jan. 7, 2010.*
Hao Li et al., "Mechanical Bond Formation by Radical Templation", Angew. Chem. int. Ed, 2010, 49, 8260-8265. Published Sep. 23, 2010.*
Hao Li et al., "A Light-Stimulated Molecular Switch Driven by Radical-Radical Interactions in Water", Angew. Chem. Int. Ed., 2011, 50, 6782-6788. Published Jun. 29. 2011.*
Mohamad Hmadeh et al., "Electrostatic Barriers in Rotaxanes and Pseudorotaxanes", Chem. Eur. J., 2011, 17, 6076-6087. Published Apr. 15, 2011.*
Adar et al., Photosensitized electron-transfer reactions in beta-cyclodextrin aqueous media: effects on dissociation of ground-state complexes, charge separation, and hydrogen evolution, J. Am. Chem. Soc., 108:4696-4700 (1986).
Allwood et al., Complexation of paraquat and diquat by a bismetaphenylene-32-crown-10 derivative, J. Chem. Soc., Chem. Commun., 14:1058-61 (1987).
Ashton et al., Complexation of diquat and paraquat by macrocyclic polyethers incorporating two dihydroxynaphthalene residues, Tetrahedron Lett., 28: 6367?70 (1987).
Ashton et al., The template-directed synthesis of cyclobis (paraquat-4,4'-biphenylene), Chem. Commun., 4:487?490 (1996).
Bird et al., Electrochemistry of the Viologens, Chem. Soc. Rev., 10: 49?82 (1981).
Bockman et al., Isolation and oxidation-reduction of methylviologen cation radicals. Novel disproportionation in charge-transfer salts by x-ray crystallography, J. Org. Chem., 55: 4127-4135 (1990).
Bruinink et al., Modified viologens with improved electrochemical properties for display applications, J. Electrochem. Soc., 124:1854-1858 (1977).
Bruinink et al., The voltammetric behavior of some viologens at SnO2 electrodes, J. Electrochem. Soc., 125, 1397-1401 (1978).
Chiang et al., A Macrocycle/Molecular-Clip Complex that Functions as a Quadruply Controllable Molecular Switch, Chem. Eur. J., 12:865?876 (2006).

(Continued)

*Primary Examiner* — Douglas McGinty

(74) *Attorney, Agent, or Firm* — Marshall, Gerstein & Borun LLP

(57) ABSTRACT

Described herein are methods of generating 4,4'-bipyridinium radical cations (BIPY$^{\cdot+}$), and methods for utilizing the radical-radical interactions between two or more BIPY$^{\cdot+}$ radical cations that ensue for the creation of novel materials for applications in nanotechnology. Synthetic methodologies, crystallographic engineering techniques, methods of physical characterization, and end uses are described.

21 Claims, 16 Drawing Sheets

(56) References Cited

OTHER PUBLICATIONS

Claude-Montigny et al., Microenvironment effects on the kinetics of electron-transfer reactions involving dithionite ions and viologens. 2. Stabilization of ion radicals by polyelectrolytes and dimerization kinetics of dialkyl viologens. J. Phys. Chem., 96, 4432-4437 (1992).

Dichtel et al., Kinetic and thermodynamic approaches for the efficient formation of mechanical bonds, Acc. Chem. Res., 41:1750-1761 (2008).

Endo et al., Viologens used "electron phase transfer". Catalytic debromination of vic-dibromides under heterophase conditions using viologens, J. Am. Chem. Soc., 106: 1124-112 (1984).

Evans et al., Bipyridyl radical cations. Part I. Electron spin resonance study of the dimerisation equilibrium of morphamquat radical cation in methanol, J. Chem. Soc., Perkin Trans., 2, 1310-1311 (1975).

Evans et al., Electron spin resonance study of the dimerization equilibrium of the radical cation of 1,1'-diethyl-4,4'-bipyridylium diiodide in methanol, J. Am. Chem. Soc., 99: 5882-5884 (1977).

Furue et al., Photoinduced two-electron reduction of methyl viologen dimer by 2-propanol through intramolecular process an formation of viologen radical cation dimer, Chem. Lett., 9: 821-824 (1980).

Gasa et al., Complexation between methyl viologen (paraquat) bis(hexafluorophosphate) and dibenzo[24]crown-8 revisited. Chem. Eur. J., 15: 106-16 (2009).

Gaudiello et al., Polymer Films on Electrodes. 17. The Application of Simultaneous Electrochemical and Electron Spin Resonance Techniques for the Study of Two Viologen-Based Chemically Modified Electrodes, J. Am. Chem. Soc., 107: 3027-3032 (1985).

Goren et al., Photochemical and chemical reduction of vicinal dibromides via phase transfer of 4,4'-bipyridinium radical: the role of radical disproportionation, J. Am. Chem. Soc., 105:7764-7765 (1983).

Gueder et al., Single and double bridged viologens and intramolecular pimerization of their cation radicals, Tetrahedron, 42:1665-1677 (1986).

Han et al., Potential-induced redox switching in viologen self-assembled monolayers: An ATR-SEIRAS approach, J. Phys. Chem. C, 111, 13855-13863 (2007).

Hwang et al., New three-way supramolecular switch based on redox-controlled interconversion of heter- and homo-guest-pair inclusion inside a host molecule, Chem. Commun. 416-418 (2008).

Hünig, Stable Radical Ions, Pure Appl. Chem., 15:109-122 (1967).

Ito et al., Infrared spectra and dimer structure of reduced viologen compounds. J. Phys. Chem., 91:3932-3934 (1987).

Jeon et al., A [2]Pseudorotaxane-Based Molecular Machine: Reversible Formation of a Molecular Loop Driven by Electrochemical and Photochemical Stimuli. Angew. Chem.,115, 4231-4234 (2003).

Jeon et al., Control of the stoichiometry in host-guest complexation by redox chemistry of guests: Inclusion of methylviologen in cucurbit[8]uril, Chem. Commun., 1828-1829 (2002).

Johnson et al., High-Resolution ESR Spectra of Photochemically Generated Free Radicals: The Viologens, J. Chem. Phys., 39:58-62 (1963).

Kim et al., Functionalized cucurbiturils and their applications. Chem. Soc. Rev., 36:267-279 (2007).

Ko et al., Supramolecular assemblies built with host-stabilized charge-transfer interactions, Chem. Commun., 1305-1315 (2007).

Kosower et al., Pyridinyl diradical pi.-mer. Magnesium iodide complexes, J. Am. Chem. Soc. 93:2534-2535 (1971).

Kosower et al., Stable free radicals. II. The reduction of 1-methyl-4-cyanopyridinium ion to methylviologen cation radical, J. Am. Chem. Soc., 86:5524-5527 (1964).

Li et al., Degenerate [2]rotaxanes with electrostatic barriers, Org. Biomol. Chem., 9:2240-50 (2011).

Meisel et al., Catalysis of methyl viologen radical reactions by polymer-stabilized gold sols. J. Phys. Chem., 85: 179-187 (1981).

Michaelis et al., The Viologen Indicators, J. Gen. Physiol., 16:859-873 (1933).

Michaelis, Semiquinones, the Intermediate Steps of Reversible Organic Oxidation-Reduction. Chem. Rev., 16:243?286 (1935).

Monk et al., Spin pairing ('dimerisation') of the viologen radical cation: kinetics and equilibria, Dyes & Pigments, 43:207-217 (1999).

Monk et al., The colours of charge-transfer complexes of methyl viologen: effects of donor, ionic strength and solvent—a lecture and reprint volume, Dyes and Pigments, 43, 241-251 (1999).

Odell et al., Cyclobis(paraquat-p-phenylene). A Tetracationic Multipurpose Receptor. Angew. Chem. Int. Ed. Engl., 27: 1547?1550 (1988).

Park et al., Facile dimerization of viologen radical cations covalently bonded to β-cyclodextrin and suppression of the dimerization by β-cyclodextrin and amphiphiles. J. Phys. Chem., 100, 769 774 (1996).

Park et al., Sodium dithionite reduction of nitroarenes using viologen as an electron phase-transfer catalyst, Tetrahedron Lett., 34, 7445-7446 (1993).

Quintela et al., Electrochemistry of methylviologen in the presence of sodium decyl sulfate, Langmuir, 3:769-773 (1987).

Stoddart, The chemistry of the mechanical bond, Chem. Soc. Rev. 38:1802-1820 (2009).

Takeshi et al., Reduction of acrylonitrile in the presence of viologen derivatives. J. Org. Chem., 51: 4309-43 (1986).

Trabolsi et al. Redox-driven switching in pseudorotaxanes. New J. Chem., 33, 254-263 (2009).

Trabolsi et al., Radically enhanced molecular recognition. Nature Chem., 2, 42?49 (2010).

van Dam et al., Electrochemically generated colored films of insoluble viologen radical compounds, J. Electrochem. Soc., 121, 1555-1558 (1974).

Yasuda et al., Electrochromic properties of alkylviologen-cyclodextrin systems. J. Appl. Electrochem., 17: 567-573 (1987).

* cited by examiner

CRYSTALLINE BIPYRIDINIUM RADICAL COMPLEXES AND USES THEREOF

CROSS-REFERENCE TO RELATED APPLICATIONS

The benefit under 35 U.S.C. §119 of U.S. Provisional Application No. 61/537,852, filed Sep. 22, 2011 is claimed, the disclosure of which is incorporated by reference in its entirety.

STATEMENT OF GOVERNMENT SUPPORT

This invention was made with U.S. government support under Grant No. DMR-0520513 awarded by the National Science Foundation; Grant No. FA9550-07-1-0534 awarded by the Air Force Office of Scientific Research (AFOSR); Grant No. W911NF-10-1-0510 awarded by the Army Research Office (ARO); and Grant No. DE-SC0005462 awarded by the Department of Energy (DOE). The government has certain rights in the invention.

FIELD OF THE INVENTION

The invention relates to molecular compounds and complexes incorporating BIPY$^{•+}$ derivatives that are made to interact by means of radical-radical interactions with the diradical dicationic cyclobis(paraquat-p-phenylene) (CBPQT$^{2(•+)}$) ring. Host-guest inclusion complexes and mechanically interlocked molecules (MIMs) are described.

BACKGROUND

The ability of BIPY$^{•+}$ radical cations to exist as stable radical cations has long been known, and their tendency to undergo dimerization [(BIPY$^{•+}$)$_2$] by means of favorable radical-radical interactions (also referred to as pimerization) well is documented. However, the stabilities of these BIPY$^{•+}$ radical cation dimers are rather weak, especially in organic solvents, which challenges their use in applications.

SUMMARY

Applicants have discovered a means to increase the stabilities of radical-radical BIPY$^{•+}$ interactions by use of host-guest chemistry utilizing the CBPQT$^{2(•+)}$ ring. This has allowed for the further development of template-directed synthetic methodologies in the construction of MIMs, and the ability to mechanically switch these MIMs by transfer of electrons. Applicants have also devised crystal engineering techniques for the production of novel solid-state materials composed of these MIMs and host-guest complexes, while in their radical cationic forms. Throughout this disclosure the BIPY guest molecule is alternatively referred to as a compound of formula (I).

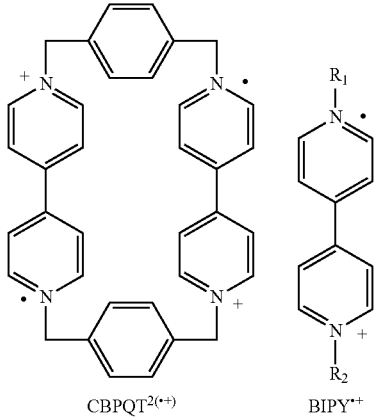

In some embodiments the BIPY$^{•+}$ guests have been alkyl derivatives, for example

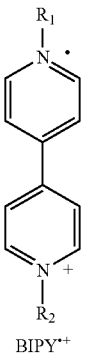

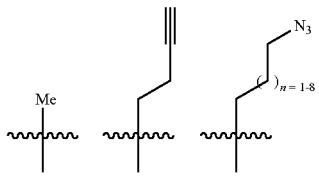

In some embodiments the BIPY$^{•+}$ guests have been aryl derivatives, for example -continued

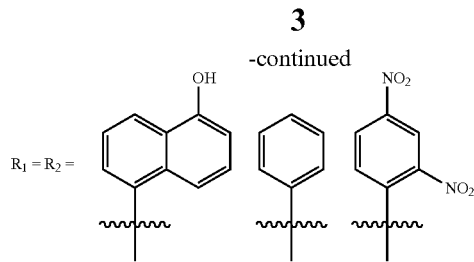

$R_1 = R_2 =$

By one method, complexation of BIPY$^{\bullet+}$ guests with the CBPQT$^{2(\bullet+)}$ ring can be induced light using the Ru(bpy)$_3^{2+}$ photosensitizer.

By one method, complexation of BIPY$^{\bullet+}$ guests with the CBPQT$^{2(\bullet+)}$ ring can be induced by chemical reduction using zinc dust.

By one method, complexation of BIPY$^{\bullet+}$ guests with the CBPQT$^{2(\bullet+)}$ ring can be induced electrochemically at the surface of an electrode.

In some MIMs with BIPY$^{\bullet+}$ and CBPQT$^{2(\bullet+)}$ ring components, switching has been induced by light using the Ru(bpy)$_3^{2+}$ photosensitizer.

In some MIMs with BIPY$^{\bullet+}$ and CBPQT$^{2(\bullet+)}$ ring components, switching has been induced chemically using zinc dust as a reducing agent.

Complexation can be performed in either water or organic solvent.

The synthesis of MIMs can be achieved using a threading-followed-by-stoppering approach.

The synthesis of MIMs can be achieved using a clipping approach.

Crystallization of complexes can be achieved using slow-vapor diffusion in MeCN with iPr$_2$O as the bad solvent under an inert atmosphere.

Crystallization of MIMs can be achieved using slow-vapor diffusion in MeCN with iPr$_2$O as the bad solvent under an inert atmosphere.

Crystallization can be carried out at concentrations ranging from 10 mM to 40 μM of the mother liquor.

DETAILED DESCRIPTION

Figure 1:
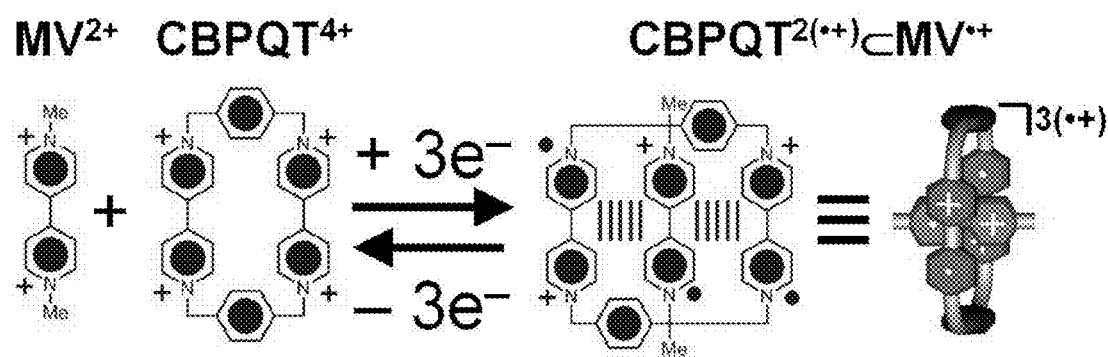
FIG. 1. Simplified schematic representation using structural formulas of the redox-induced formation of the trisradical cationic inclusion complex CBPQT$^{2(\bullet+)}$ ⊂ MV$^{\bullet+}$ and its graphical representation. Upon a three-electron reduction of an equimolar mixture of CBPQT$^{4+}$ and MV$^{2+}$, the MV$^{\bullet+}$ radical cation is included spontaneously inside the cavity of the CBPQT$^{2(\bullet+)}$ diradical dication ring as a result of favorable radical-radical interactions occurring between the three BIPY$^{\bullet+}$ radical cations. Re-oxidation of the tricationic complex results in the regeneration of the initial uncomplexed CBPQT$^{4+}$ host and MV$^{2+}$ guest.

Disclosed herein are complexes of CBPQT$^{2(\cdot+)}$ and a guest molecule, e.g., a compound of formula (I):

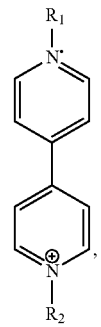

(I)

R$^1$ and R$^2$ are each independently selected from alkyl, cycloalkyl, heterocycloalkyl, aryl, heteroaryl, alkenyl, alkynyl, alkyleneazido, alkylenecycloalkyl, alkyleneheterocycloalkyl, or alkylenearyl. Each R$^1$ and R$^2$ can be the same or different. Choice of steric and electronic properties of the R groups can influence the end properties of the complex. For example, the complex can be tuned by these selections to provide a complex with a particular conductance, redox potential, and/or UV-vis property.

These complexes can be isolated as crystals, e.g., single crystal, structures. The complex also has a single unpaired electron which can allow for control of crystal growth of the complex by application of an external magnetic field. This single unpaired electron is stable because it is delocalized over the whole complex. Since host-guest chemistry is used prior to crystal growth, it allows for creation of a large variety of materials by inserting different guests, with different electronic properties into the host. In this way the electronic properties of the material (crystal) can be tuned in a very modular way.

Synthesis of Compounds of Formula (I)

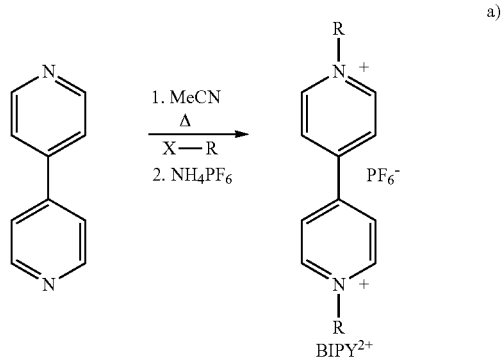

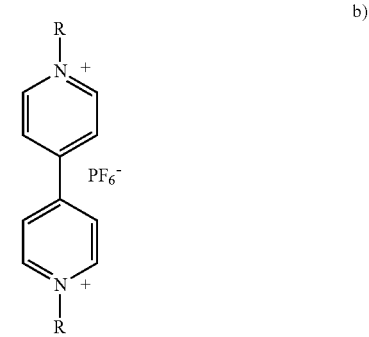

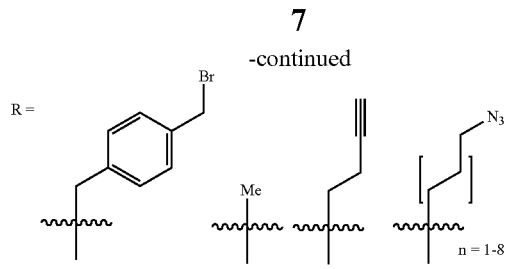

Symmetric 1,1'-dialkyl-4,4'-bipyridinium derivatives can be synthesized in one step starting from 4,4'-bipyridine and an alkyl derivative functionalized with a good leaving group (X), e.g., chloro, bromo, iodo, tosyl, mesyl, etc. In general, the syntheses are performed in refluxing acetonitrile in the presence of two or more equivalents of the alkyl derivative functionalized with the good leaving group. Isolation of the target does not require column chromatography in most cases. After the reaction has come to completion, the acetonitrile can be removed to a minimal volume, and the residual solid is converted to its $PF_6^-$ salt by addition of an aqueous solution of $NH_4PF_6$. The resulting water insoluble salt is filtered, washed with water leaving behind the target product in pure form and ready to use in the next step. Using this synthetic methodology, the viologen derivatives shown above have been synthesized.

Asymmetric 1-alkyl-1'-alkyl'-4,4'-bipyridinium derivatives can be synthesized in two steps. Generally the reactions are carried out in refluxing acetonitrile. The first step begins with a slight excess of 4,4'-bipyridine (2-5 equivalents) and one equivalent of the alkyl functionalized with a good leaving group. After the reaction comes to completion, the solvent is reduced to a minimal volume, followed by addition of an aqueous solution of $NH_4PF_6$. The resulting precipitate is collected by filtration and washed with water, and then by ether to remove the excess 4,4'-bipyridine. The monofunctionalized bipyridine is then ready to use in the next step. It is dissolved in refluxing acetonitrile along with the other alkyl group functionalized with a good leaving group. After the reaction has come to completion, the solvent is reduced to a minimal volume, and an aqueous solution of $NH_4PF_6$ is added. The resulting precipitate is collected by filtration and washed with water to yield the product in pure form. Using this synthetic methodology, the asymmetric viologen derivatives have been synthesized.

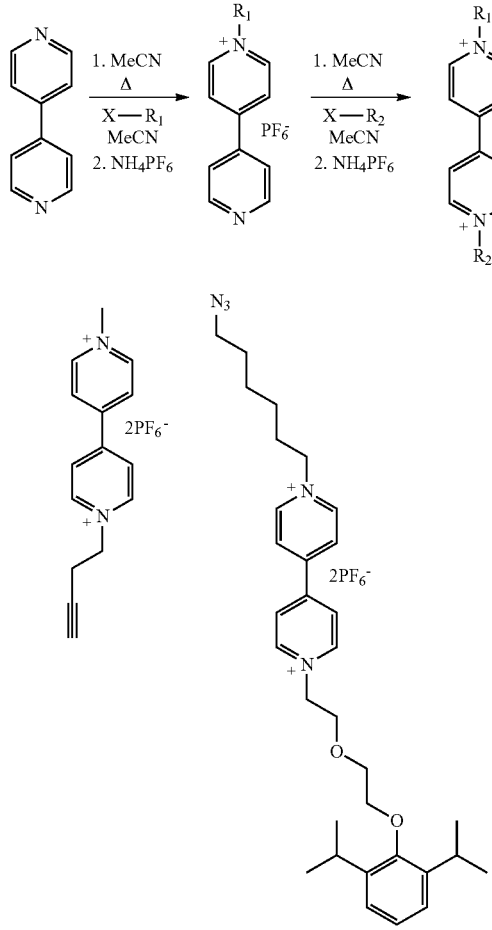

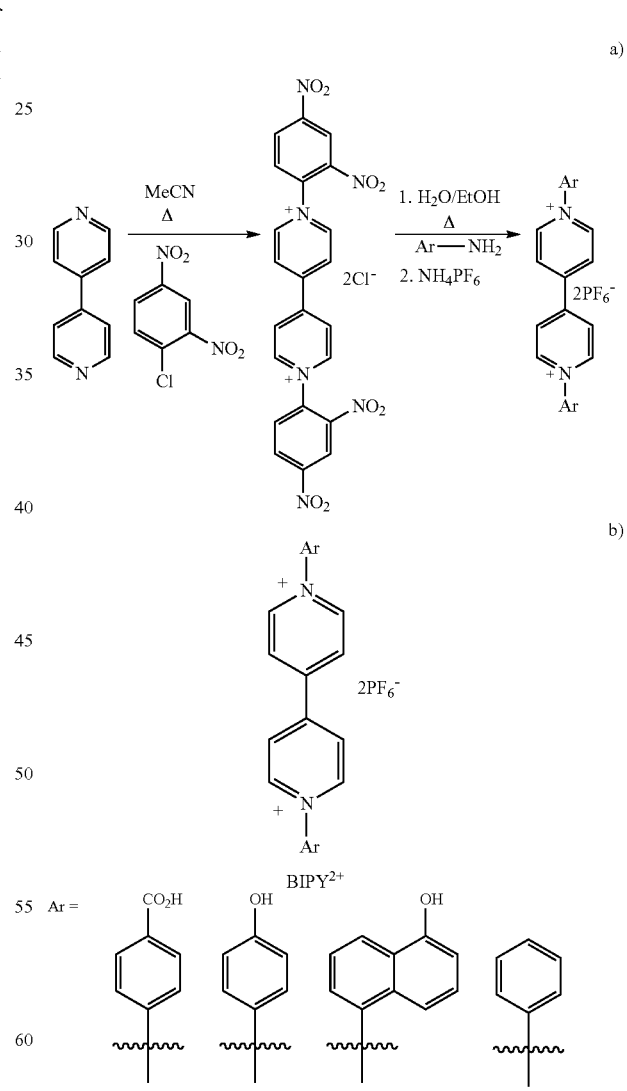

Symmetric 1,1'-diaryl-4,4'-bipyridinium derivatives can be synthesized in two steps. Starting from 4,4'-bipyridinium and two or more equivalents of 1-chloro-2,4-dinitrobenzene, the mixture is allowed to reflux in acetonitrile for at least three days. After this time, the reaction is allowed to cool to room temperature, and the precipitate is collected and washed with additional acetonitrile to remove any excess 1-chloro-2,4-dinitrobenzene. The resulting chloride salt of 1,1'-bis(1,4-dinitrobenzene)-4,4'-bipyridinium is ready to use in the next step. It is dissolved in a mixture of ethanol and water along with the desired aryl amine derivative and heated to reflux for a few days. The reaction proceeds by a Zincke mechanism, releasing 1,4-dinitroaniline as a side product. After the reaction has come to completion, the reaction is filtered in order to remove excess aniline starting material as well as the side product. The solvent is then reduced to a minimal level, and an aqueous solution of $NH_4PF_6$ is added. The resulting precipitate is collected by filtration and washed with water and ether to afford the target product in pure form. The symmetric 1,1'-diaryl-4,4'-bipyridinium shown above have been synthesized in this manner.

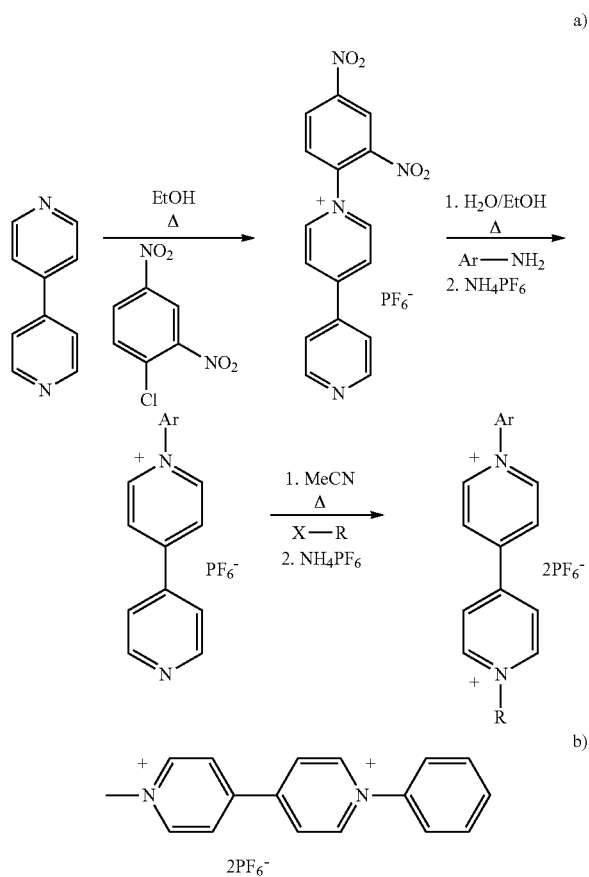

Asymmetric 1-alkyl-1'-aryl-4,4'-bipyridinium derivatives can be synthesized in three steps. Starting with a slight excess of 4,4'-bipyridine and one equivalent of 1-chloro-2,4-dinitrobenzene, the mixture is allowed to react for a few days in refluxing ethanol. The solvent is reduced to a minimal volume, and to it is added an excess of ether. The resulting precipitate is collected by filtration to yield the target monofunctionalized bipyridine in pure form. Next, it is dissolved in an ethanol water mixture along with the desired aryl amine in order to undergo a Zincke reaction. The solvent is reduced to a minimal volume and filtered in order to remove excess aniline starting material and side product. To the filtrate is added an aqueous solution of $NH_4PF_6$, and the resulting precipitate is collected by filtration and washed with water. The monofunctionalized aryl derivative is ready to use in the next step. It is dissolved in refluxing acetonitrile along with an alkyl derivative functionalized with a good leaving group. After a few days, the solvent is reduced to a minimal level, and an aqueous solution of $NH_4PF_6$ is added. The resulting precipitate is collected by filtration and washed with water and ether, yielding the asymmetric 1-alkyl-1'-aryl-4,4'-bipyridinium in pure form. Using this synthetic methodology, the asymmetric viologen derivative shown above has been synthesized.

Mechanism of Complex Formation

The chemical formulas and graphical representations of the trisradical tricationic $CBPQT^{2(\cdot+)} \subset MV^{\cdot+}$ complex along with the simplified schematic of the redox-induced complexation processes are illustrated in FIG. 1. Following a three-electron reduction, with two electrons, one going into each of the two $BIPY^{2+}$ subunits of the $CBPQT^{4+}$ ring, and one electron going to the $BIPY^{2+}$ unit of the $MV^{2+}$ guest, a stable thermodynamic state arises whereby the $CBPQT^{2(\cdot+)}$ ring is made to encircle the $MV^{\cdot+}$ radical cation. We have shown both experimentally and theoretically that as a result of the fact that only two of the $BIPY^{\cdot+}$ radical cations of the complex are spin paired at a given time, the third unpaired $BIPY^{\cdot+}$ radical cation of the complex is not as strongly engaged in radical-radical interactions. This fact has important consequences for the redox-induced mechanism of switching, which will be discussed in detail in this paper. Re-oxidation of the complex results in its dissociation into its constituent components. Overall, the complexation is reversible.

In a 1:1 mixture of $CBPQT^{4+}$ and $MV^{2+}$, both in their fully oxidized forms, no binding between the two is observed to occur, as a consequence of their similar π-electron-poor natures, not to mention electrostatic repulsion. Upon a three-electron reduction, with two electrons transferred forming the $CBPQT^{2(\cdot+)}$ ring and one forming the $MV^{\cdot+}$ guest, formation of the trisradical $CBPQT^{2(\cdot+)} \subset MV^{\cdot+}$ inclusion complex ensues promptly as a result of favorable radical-radical interactions—all of which can be stimulated electrochemically.

The nature of these radical-radical interactions is largely a consequence of radical pairing, a phenomenon that has been well studied in the case of the classical viologen radical cation dimers and violenes in general, of which are EPR silent (paired) but are once again active in their monomeric (unpaired) form. This mechanistic feature of radical pairing has important implications when considering the electrochemical behavior of the trisradical $CBPQT^{2(\cdot+)} \subset MV^{\cdot+}$ complex. Consider the hypothesis that only two of the $BIPY^{\cdot+}$ radical cation subunits of the complex are paired at any one time leaving one $BIPY^{\cdot+}$ radical cation subunit of the $CBPQT^{2(\cdot+)}$ ring unpaired. As a result, this unpaired $BIPY^{\cdot+}$ unit is not as strongly engaged in radical-radical interactions as the other two paired $BIPY^{\cdot+}$ units. Theoretical investigations based on DFT to calculate the singly occupied molecular orbital (SOMO) of the trisradical $CBPQT^{2(\cdot+)} \subset MV^{\cdot+}$ complex support the hypothesis, by revealing that orbital overlap of the $MV^{\cdot+}$ guest occurs predominantly with only one of the $BIPY^{\cdot+}$ units in the $CBPQT^{2(\cdot+)}$ ring. The fact that one $BIPY^{\cdot+}$ radical cation in the ring is not as strongly interactive with the $MV^{\cdot+}$ guest mandates, from a thermodynamic perspective, that this unpaired $BIPY^{\cdot+}$ unit undergoes reduction to its neutral $BIPY^0$ form at a less negative potential, i.e., easier to reduce—in comparison to the two radically paired $BIPY^{\cdot+}$ units. The logical corollary to this is that the re-oxidation of the unpaired $BIPY^{\cdot+}$ radical cation unit should occur at more negative potentials—i.e., easier to oxidize—compared to the two paired $BIPY^{\cdot+}$ radical cation units. It follows then that the formation of a tetracationic $CBPQT^{(2+)(\cdot+)} \subset MV^{\cdot+}$ bisradical inclusion complex must appear in the electrochemical switching mechanism.

Figure 2:
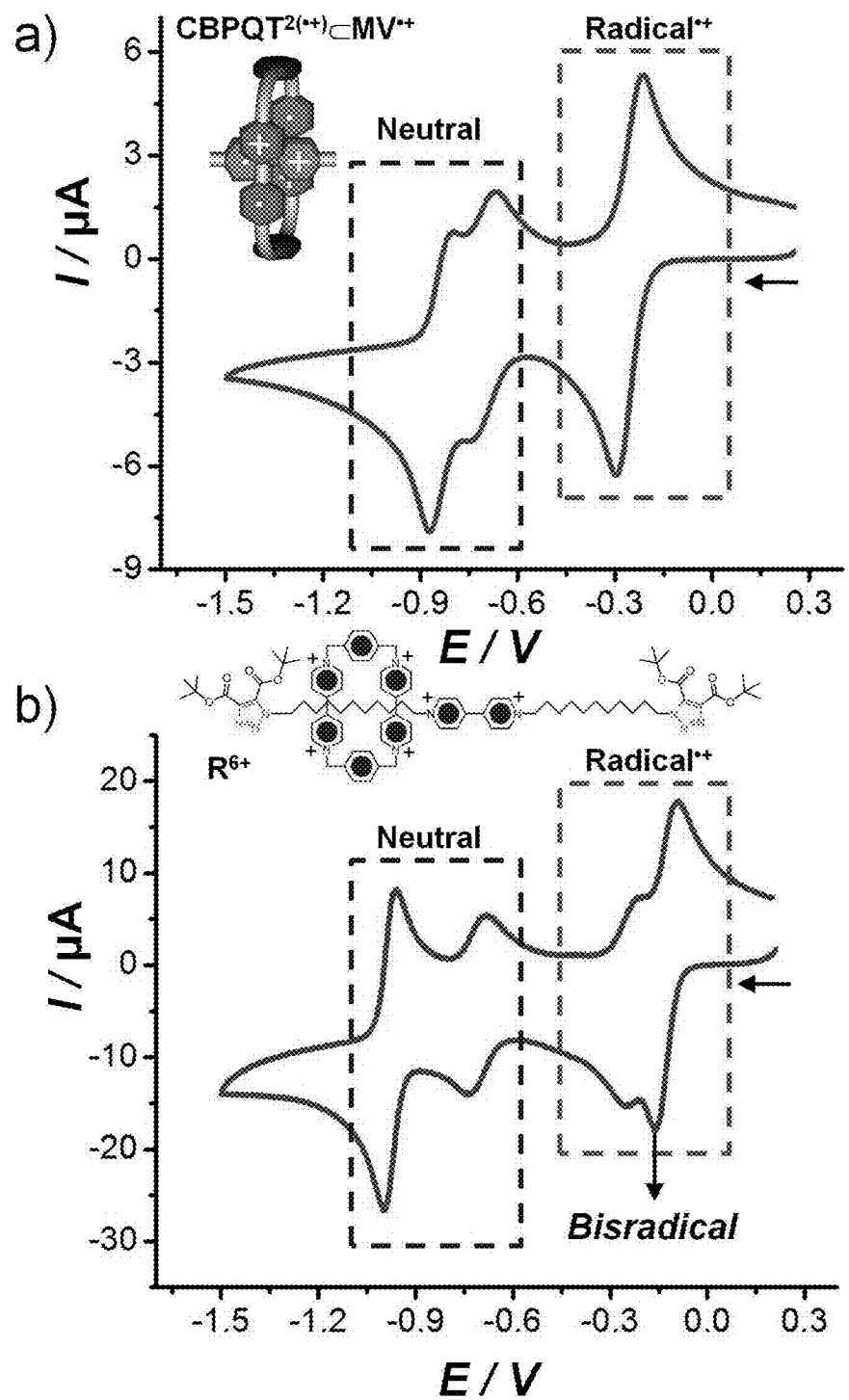
FIG. 2. a) Cyclic voltammogram of an equimolar mixture of CBPQT$^{4+}$ and MV$^{2+}$ in MeCN at 1.0 mM. The first reduction process is a three-electron one leading to the formation of the trisradical CBPQT$^{2(\bullet+)}$ ⊂ MV$^{\bullet+}$ inclusion complex. As a consequence of radical pairing between one BIPY$^{\bullet+}$ of the ring and that from MV$^{\bullet+}$, the reduction of the complex is observed to occur over, first by a one-electron process, followed by a two-electron one—the former (and less negative) one is assigned to the reduction of the unpaired BIPY$^{\bullet+}$ unit in the ring. b) Cyclic voltammogram of the [2]rotaxane R$^{6+}$ containing only a BIPY$^{2+}$ recognition unit in its dumbbell component. As a consequence of both radical pairing and the mechanical bond, the first reduction processes leading to the trisradical species R$^{3(\bullet+)}$ is observed to occur over, first by a two-electron process, followed by a one-electron one. The first two-electron process is assigned to the simultaneous reduction of one BIPY$^{2+}$ unit of the ring and the BIPY$^{2+}$ unit of the dumbbell component, leading to the formation of a stable bisradical intermediate. Both voltammograms were recorded at a scan rate of 200 mV s$^{-1}$.

The cyclic voltammogram (CV) of an equimolar mixture of the $CBPQT^{4+}$ ring and $MV^{2+}$ is illustrated in FIG. 2a. The first reduction peak is a three-electron process with two electrons going to $CBPQT^{4+}$, forming the diradical dication $CBPQT^{2(\cdot+)}$, and one electron going to $MV^{2+}$, forming the radical cation $MV^{\cdot+}$. As a result of this three-electron process, formation of the trisradical tetracationic inclusion complex ensues electrochemically. The result of this interaction is that only one of the BIPY•+ radical cations of the complexed $CBPQT^{2(\cdot+)}$ interacts strongly with the $MV^{\cdot+}$ radical cation, such that the second reduction of this weakly interacting, unpaired $BIPY^{\cdot+}$ occurs at a less negative potential—roughly at the same potential as the second reduction of $CBPQT^{4+}$ alone in solution—while the second reduction of the $BIPY^{\cdot+}$ of the complexed $CBPQT^{2(\cdot+)}$, paired with the $MV^{\cdot+}$ radical cation, occurs simultaneously at a more negative potential as a two-electron process.

The [2]rotaxane $R^{6+}$ (FIG. 2b) composed of a $CBPQT^{4+}$ ring mechanically interlocked around a dumbbell containing a $BIPY^{2+}$ unit, was obtained using a threading-followed-by-stoppering template-directed protocol relying upon radical-radical interactions and employing a copper-free 1,3-dipolar cycloaddition in the final reaction step, which leads to the formation of the mechanical bond. As a consequence of the mechanical bond, the $CBPQT^{4+}$ ring cannot escape the influences of the $BIPY^{2+}$ unit in the dumbbell component entirely. In such a situation, both the trisradical and bisradical forms of the rotaxane are stable species. Electrochemical experiments reveal that reduction to the trisradical tricationic form of the rotaxane $R^{3(\cdot+)}$ occurs over two different electron-transfer processes. The first is a two-electron reduction process, which is assigned to the formation of the spin-paired $BIPY^{\cdot+}$ radical cation of the dumbbell with one from the ring forming the bisradical tetracationic $R^{2(\cdot+)(2+)}$. The subsequent one-electron transfer is assigned to the reduction of the remaining unpaired $BIPY^{2+}$ in the $CBPQT^{2(\cdot+)}$ ring, a process which generates the trisradical tricationic $R^{3(\cdot+)}$ form of the rotaxane. Both of these redox processes are independent of the scan rate, i. e., they are totally reversible as a consequence of the fact that the mechanical bond excludes the possibility of dissociation and so serves to stabilize the bisradical form of the rotaxane in comparison to that of its bisradical tetracationic $CBPQT^{(2+)(\cdot+)} \subset MV^{\cdot+}$ supramolecular analogue.

Figure 3:
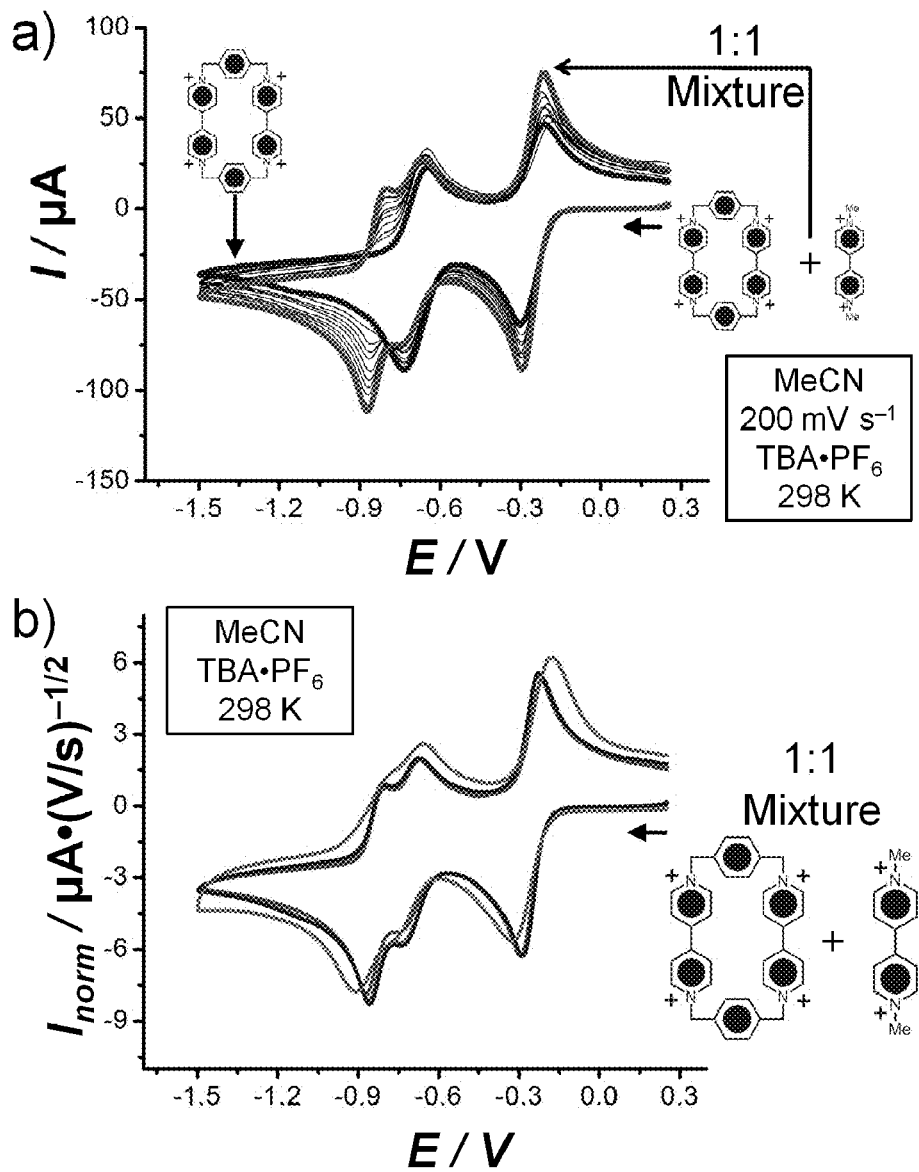
FIG. 3. a) A CV titration of a solution of MV$^{2+}$ (10 mM) into a solution of CBPQT$^{4+}$ (1.0 mM) in MeCN at 298 K. Blue trace: CBPQT$^{4+}$ only. Purple trace: 1:1 mixture of CBPQT$^{4+}$ and MV$^{2+}$. b) Variable scan rate CVs of the 1:1 mixture of CBPQT$^{4+}$ and MV$^{2+}$ in MeCN at 298 K. Blue trace: 200 mV s$^{-1}$; red trace: 1000 mV s$^{-1}$; pink trace: 30 V s$^{-1}$.

In an effort to detect the bisradical tetracationic $CBPQT^{(2+)(\cdot+)} \subset MV^{\cdot+}$ inclusion complex, variable scan rate CV experiments were carried out initially on a 1:1 mixture of $CBPQT^{4+}$ and $MV^{2+}$. They revealed (FIG. 3), however, that the re-oxidation of the trisradical tricationic complex of $CBPQT^{2(\cdot+)} \subset MV^{\cdot+}$ is independent (up to 30 Vs$^{-1}$) of scan rate. This observation suggests that dissociation of $CBPQT^{(2+)(\cdot+)} \subset MV^{\cdot+}$ is too fast to detect on the timescale of the CV experiments. In order to probe the nature of the bisradical tetracationic intermediate, we performed variable scan rate CV experiments on a 1:1 mixture of $CBPQT^{4+}$ and $V^{2+}$, where the butynyl functions act to slow down the rate of dissociation such that the intermediate can be more readily observed under the experimental setup employed. We hypothesize that the extra steric bulk and/or favorable noncovalent bonding interactions resulting from the presence of the butynyl substituents of $V^{2+}$ act to stabilize the bisradical tetracationic intermediate kinetically $CBPQT^{(2+)(\cdot+)} \subset V^{\cdot+}$ in comparison to the methyl groups of $MV^{2+}$.

Figure 4:
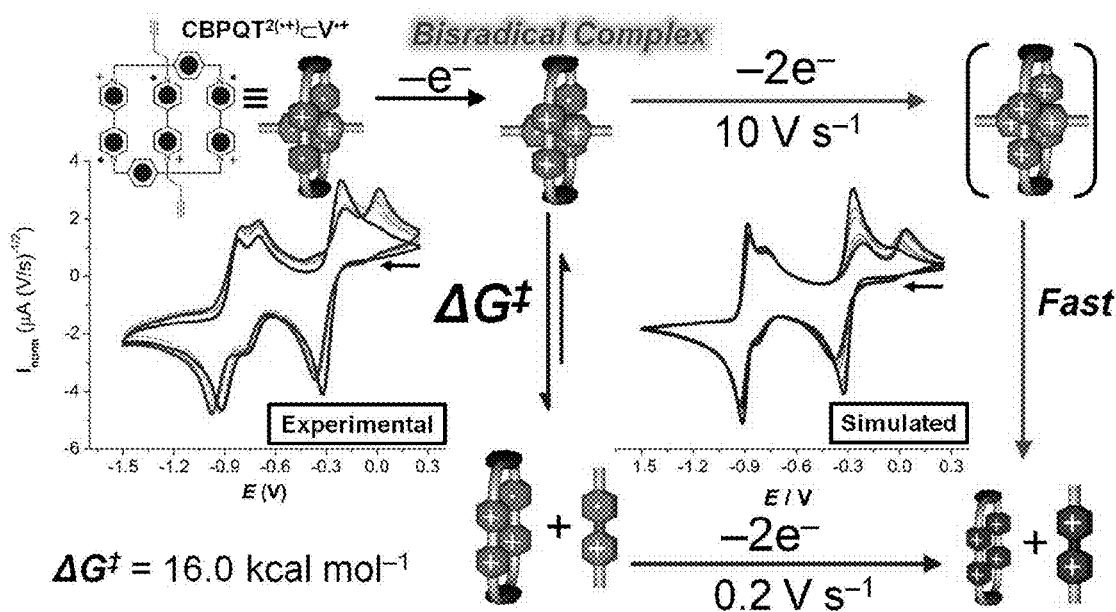
FIG. 4. Experimental and simulated variable scan rate cyclic voltammograms of a 1:1 mixture of CBPQT$^{4+}$ and V$^{2+}$ in MeCN at 298 K. As a consequence of radical pairing, one of the BIPY$^{\bullet+}$ radical cation units is oxidized first (at a less negative potential) during the scan, leading to the formation of the bisradical CBPQT$^{(2+)(\bullet+)}$ ⊂ V$^{\bullet+}$ intermediate. The presence of the BIPY$^{2+}$ unit in the CBPQT$^{(2+)(\bullet+)}$ ring leads to dissociation of the complex observable on the timescale of the CV experiments. Fitting the experimental data to the digital simulations, the free energy barrier ΔG$^{‡}$ to dissociation of the bisradical CBPQT$^{(2+)(\bullet+)}$ ⊂ V$^{\bullet+}$ complex was determined to be 16.0 kcal mol$^{-1}$. Blue trace=200 mV s$^{-1}$; purple trace=10 V$^{-1}$. IR compensation was applied.

Evidence for the existence of $CBPQT^{(2+)(\cdot+)} \subset V^{\cdot+}$ inclusion complex in solution can be obtained (FIG. 4) from variable scanrate CV in MeCN. As a consequence of the presence of the dicationic $BIPY^{2+}$ unit, the bisradical $CBPQT^{(2+)(\cdot+)} \subset V^{\cdot+}$ complex forfeits a substantial amount of stability compared to the trisradical $CBPQT^{2(\cdot+)} \subset V^{\cdot+}$ complex. The $CBPQT^{(2+)(\cdot+)} \subset V^{\cdot+}$ begins to dissociate into is individual components, making re-oxidation of the two remaining $BIPY^{\cdot+}$ radical cations of the separate host and guest components occur at a more negative (easier to re-oxidize) potential. When scanning at a rate slower than the timescale of the dissociation of the $CBPQT^{(2+)(\cdot+)} \subset V^{\cdot+}$, re-oxidation of the trisradical tricationic complex is observed to occur as a single, broad oxidation wave. When performing the re-oxidation at progressively faster scan rates—eventually reaching a point where dissociation of the $CBPQT^{(2+)(\cdot+)} \subset V^{\cdot+}$ is slow on the CV timescale—re-oxidation of the trisradical tricationic complex is observed to occur over (i) a one-electron transfer, followed (ii) by another two-electron transfer—the latter of which occurs at a potential shifted to almost 0 V! The first one-electron oxidation, leading to the formation of $CBPQT^{(2+)(\cdot+)} \subset V^{\cdot+}$ is assignable to the unpaired $BIPY^{\cdot+}$ subunit of the trisradical trication complex, which is more weakly engaged in radical-radical interactions. The second, dramatically shifted two-electron process, can be assigned to the simultaneous two-electron oxidation of the radically paired $BIPY^{\cdot+}$ units of $CBPQT^{(2+)(\cdot+)} \subset V^{\cdot+}$, leading to the fully oxidized and highly unstable hexacationic $CBPQT^{4+} \subset V^{2+}$ complex, which quickly dissociates on the timescale of the CV experiment.

Figure 5:
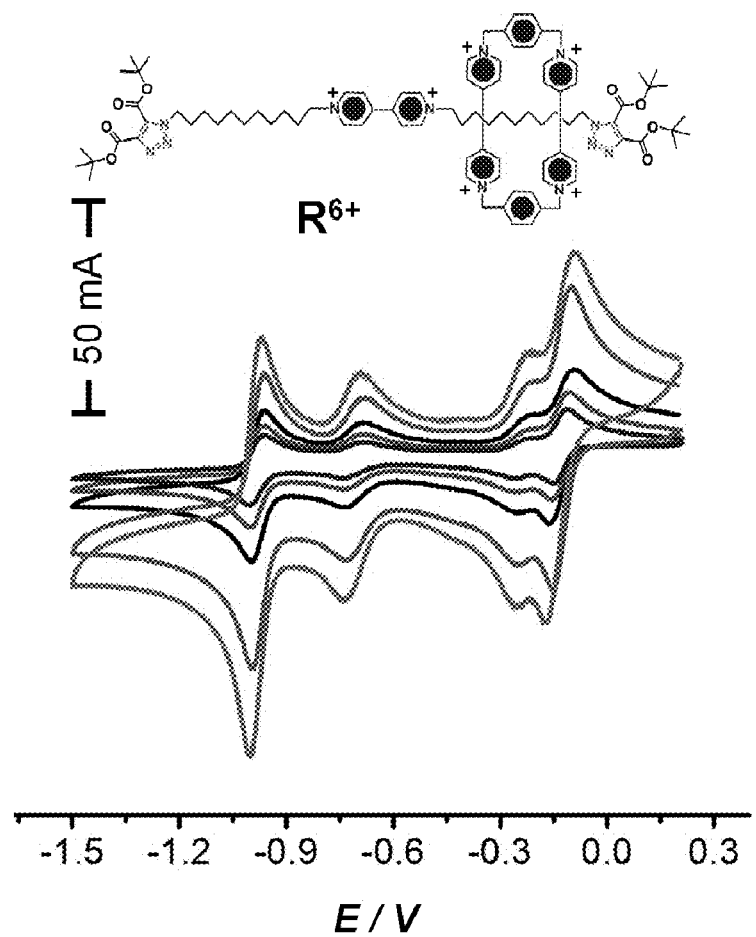
FIG. 5. Variable scan rate cyclic voltammetry of the [2]rotaxane R$^{6+}$ obtained in MeCN at 298 K with 0.1 M TBA•PF$_6$ as the supporting electrolyte. Blue trace: 50 mV s$^{-1}$; red trace: 100 mV s$^{-1}$; black trace: 200 mV s$^{-1}$; green trace: 600 mV s$^{-1}$; pink trace: 1000 mV s$^{-1}$.

As a consequence of the disassociation of the $CBPQT^{(2+)(\cdot+)} \subset V^{\cdot+}$ inclusion complex, we hypothesize that the re-oxidation potentials for both separated components become shifted to more negative potentials—resembling those of the free components alone in solution—than the first one-electron oxidation of the unpaired $BIPY^{\cdot+}$ radical cation in the scan, resulting in a single broad re-oxidation peak. Mechanistically, we propose a first-order rate law for the dissociation of the $CBPQT^{(2+)(\cdot+)} \subset V^{\cdot+}$ inclusion complex into its individual components that is proportional to a rate constant and the concentration of the bisradical species. As a control, the rotaxane $R^{6+}$ containing the $CBPQT^{4+}$ ring and a dumbbell incorporating only a $BIPY^{2+}$ unit was also investigated (FIG. 5) by variable scan rate CV. The [2]rotaxane $R^{6+}$ shows no variable scan rate dependent behavior.

Figure 6:
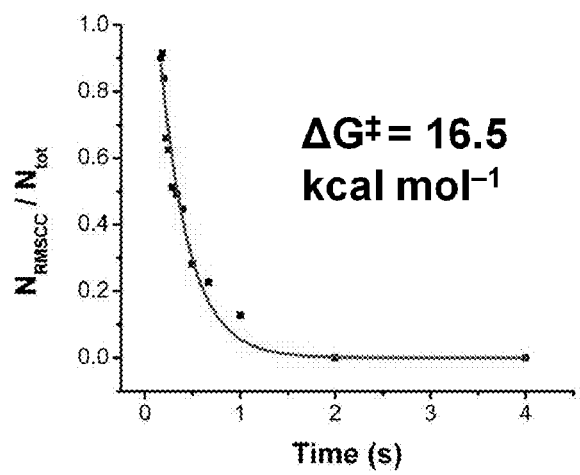
FIG. 6. Relative integration analysis of the dissociation of the bisradical complex CBPQT$^{(2+)(\bullet+)}$ ⊂ V$^{\bullet+}$ into its free components based on variable scan rate CV data shown in FIG. 4.

Digital CV simulations of the proposed mechanism were performed (FIG. 4), based on the results obtained from ITC and stopped-flow spectroscopy, and are in good agreement with the experimental data. Comparisons against digital simulations to the experimental data using a $X^2$ fitting algorithm, or by employing a relative integration analysis (FIG. 6) of the re-oxidation waves as a function of time (scanrate) the barrier governing the first-order dissociation of the bisradical dicationic complex is established to be 16.0 kcal mol$^{-1}$ or 16.5 kcal mol$^{-1}$, respectively at room temperature. Table 1 summarizes the kinetic parameters obtained from stopped-flow UV/Vis spectroscopic and CV data. It is worthy to note, that since the kinetic re-oxidation pathway of the trisradical tricationic complex is scan rate dependent, it represents an example of a bilabile system.

BIPY Guest Compound

The complexes described herein are guest-host type complexes, and comprise a $CBPQT^{2(\cdot+)}$ and a $BIPY^{\cdot+}$ compound of formula (I):

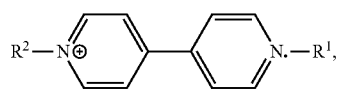

(I)

wherein the complex has a 3+ charge and three radicals, and R¹ and R² are each independently selected from alkyl, cycloalkyl, heterocycloalkyl, aryl, heteroaryl, alkenyl, alkynyl, alkyleneazido, alkylenecycloalkyl, alkyleneheterocycloalkyl, or alkylenearyl, or a salt thereof. The BIPY can have a +charge and radical, and the CBPQT a 2+ charge and two radicals.

Selection of the R¹ and R² allow for tunability of the complex properties, for example, by modifying the electron withdrawing and donating characteristics of the R groups. The choice of R groups will influence the resulting conductance, redox potential, and UV-vis characteristics of the complexes.

Some specific compounds contemplated include, but are not limited to

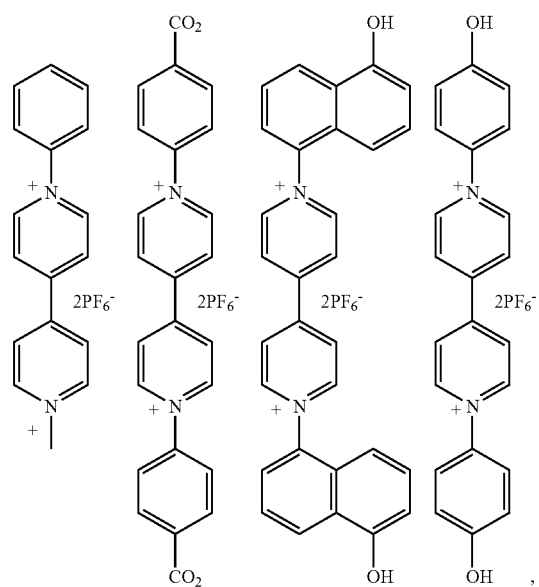

(shown before reduction to the cation radical form). Some specific R groups for the compound of formula (I) include

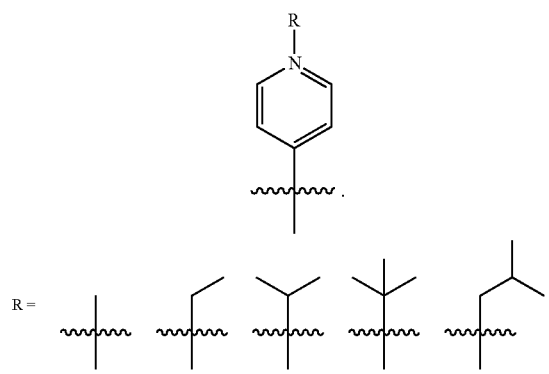

These are but only a few representative examples of the possible alkyl groups. Other examples include where the above functional groups have been modified by halogens in some position(s), with hydroxyl groups, with carboxylates, with esters, with amines, with amides, with azides, and with ethers. The limitation to the alkyl-based substitution occurs when the alkyl chains becomes so long that the large degree of freedom associated with rotation about the $sp^3$ C—C bonds prevents efficient crystallization from occurring.

Possible aryl substituents to the 4,4' positions of bipyridine are shown below and include phenyl, naphthyl, and pyrenyl derivatives. Upon these aryl substituents, additional functional groups of either electron-donating or electron-withdrawing natures may be covalently attached. By varying the electron-donating or electron withdrawing functional groups, the electronic and UV/spectroscopic properties of the substrate can be tuned to fit the needs of the given application. These functional groups are shown below, and more than one or different combinations of them may be imposed on the aryl substituents. The limitation to this functionalization occurs when the resulting dimensions of the functionalized aryl-substituent becomes sterically too large such that threading of the $CBPQT^{2(\bullet+)}$ ring can no longer occur.

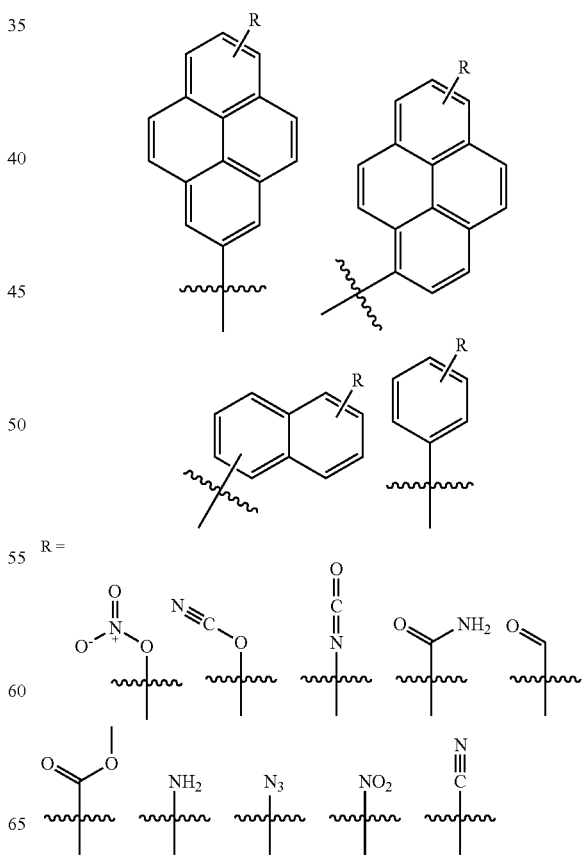

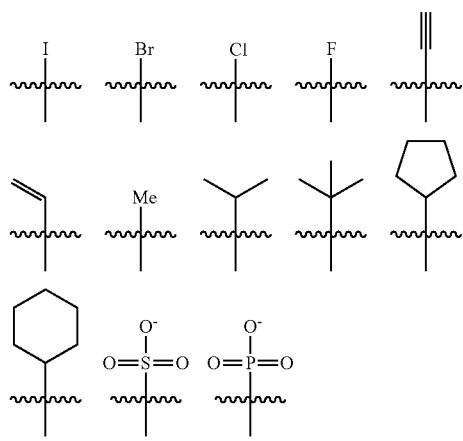

In consideration that the approximate dimensions of the CBPQT$^{2(•+)}$ ring are approximately 10 Å×7 Å, the following functionalized aryl substituents represent the limit of steric bulk imposed such that anything sterically larger will prevent the CBPQT$^{2(•+)}$ from threading.

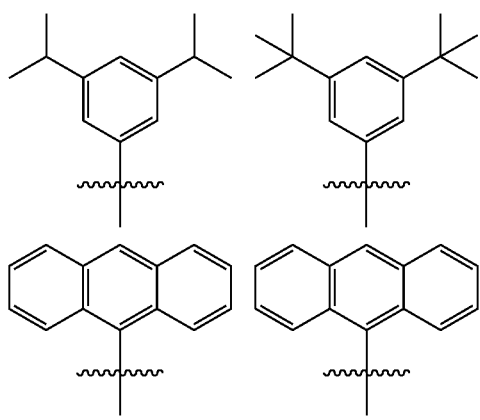

The following are examples of functionalized aryl substituents which are above the steric limit for threading of the CBPQT$^{2(•+)}$ from to occur.

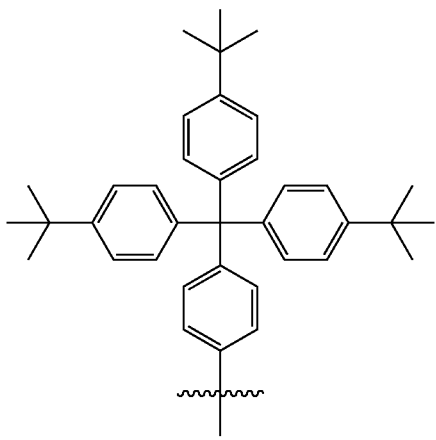

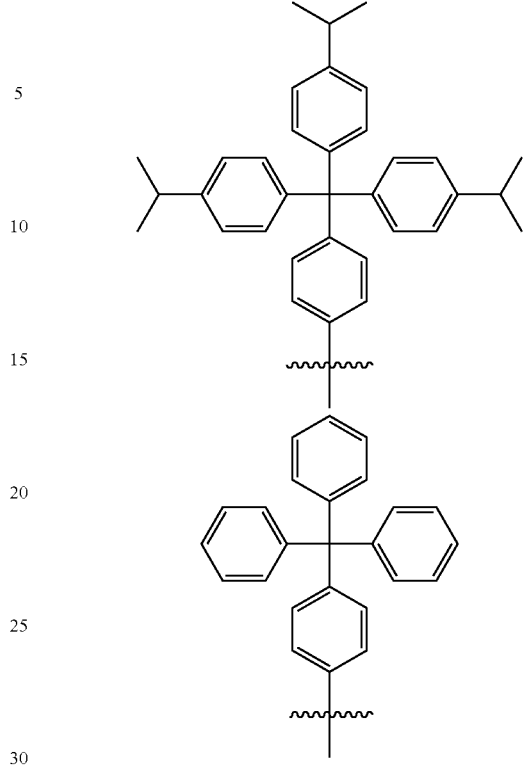

In these specific cases, a clipping mechanism must be pursued rather than a threading mechanism in order to see the CBPQT$^{2(•+)}$ encircled around the central BIPY$^{•+}$ core.

The term "alkyl" used herein refers to a saturated or unsaturated straight or branched chain hydrocarbon group of one to forty carbon atoms, including, but not limited to, methyl, ethyl, n-propyl, isopropyl, n-butyl, isobutyl, tert-butyl, n-hexyl, and the like. Alkyls of one to six carbon atoms are also contemplated. The term "alkyl" includes "bridged alkyl," i.e., a bicyclic or polycyclic hydrocarbon group, for example, norbornyl, adamantyl, bicyclo[2.2.2]octyl, bicyclo[2.2.1] heptyl, bicyclo[3.2.1]octyl, or decahydronaphthyl. Alkyl groups optionally can be substituted, for example, with hydroxy (OH), halide, thiol (SH), aryl, heteroaryl, cycloalkyl, heterocycloalkyl, and amino. It is specifically contemplated that in the compounds described herein the alkyl group consists of 1-40 carbon atoms, preferably 1-25 carbon atoms, preferably 1-15 carbon atoms, preferably 1-12 carbon atoms, preferably 1-10 carbon atoms, preferably 1-8 carbon atoms, and preferably 1-6 carbon atoms. "Heteroalkyl" is defined similarly as alkyl, except the heteroalkyl contains at least one heteroatom independently selected from the group consisting of oxygen, nitrogen, and sulfur.

As used herein, the term "cycloalkyl" refers to a cyclic hydrocarbon group, e.g., cyclopropyl, cyclobutyl, cyclohexyl, and cyclopentyl. "Heterocycloalkyl" is defined similarly as cycloalkyl, except the ring contains one to three heteroatoms independently selected from the group consisting of oxygen, nitrogen, and sulfur. Nonlimiting examples of heterocycloalkyl groups include piperdine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected from the group consisting of alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylenearyl, or alkyleneheteroaryl.

The term "alkenyl" used herein refers to a straight or branched chain hydrocarbon group of two to ten carbon atoms containing at least one carbon double bond including, but not limited to, 1-propenyl, 2-propenyl, 2-methyl-1-propenyl, 1-butenyl, 2-butenyl, and the like. The term "cycloalkenyl" refers to a cycloalkyl group having one or more double bonds. "Heterocycloalkenyl" refers to a cycloalkenyl group having one or more heteroatoms (e.g., N, S, O, or combinations thereof).

The term "alkynyl" used herein refers to a straight or branched chain hydrocarbon group of two to ten carbon atoms containing at least one carbon triple bond including, but not limited to, 1-propynyl, 2-propynyl, 1-butynyl, 2-butynyl, and the like.

The term "halide" or "halo" used herein refers to fluoro, chloro, bromo, or iodo.

The term "alkylene" used herein refers to an alkyl group having a substituent. For example, the term "alkylene aryl" refers to an alkyl group substituted with an aryl group. The alkylene group is optionally substituted with one or more substituent previously listed as an optional alkyl substituent. For example, an alkylene group can be —CH$_2$CH$_2$— or —CH$_2$—.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, OCF$_3$, NO$_2$, CN, NC, OH, alkoxy, amino, CO$_2$H, CO$_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, OCF$_3$, NO$_2$, CN, NC, OH, alkoxy, amino, CO$_2$H, CO$_2$alkyl, aryl, and heteroaryl. In some cases, the heteroaryl group is substituted with one or more of alkyl and alkoxy groups. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "alkoxy" used herein refers to straight or branched chain alkyl group covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "thioalkyl" used herein refers to one or more thio groups appended to an alkyl group.

The term "thioether" used herein refers to straight or branched chain alkyl or cycloalkyl group covalently bonded to the parent molecule through an —S— linkage. Examples of thioether groups include, but are not limited to, —SCH$_3$, —SCH$_2$CH$_3$, —SCH$_2$CH$_2$CH$_3$, —SCH(CH$_3$)$_2$, —SCH$_2$CH$_2$CH$_2$CH$_3$, —SCH$_2$CH(CH$_3$)$_2$, —SC(CH$_3$)$_3$ and the like.

The term "hydroxyalkyl" used herein refers to one or more hydroxy groups appended to an alkyl group.

The term "azide" refers to a —N$_3$ group. The term "nitro" refers to a —NO$_2$ group.

The term "amino" as used herein refers to —NR$_2$, where R is independently hydrogen, optionally substituted alkyl, optionally substituted heteroalkyl, optionally substituted cycloalkyl, optionally substituted heterocycloalkyl, optionally substituted aryl or optionally substituted heteroaryl. Non-limiting examples of amino groups include NH$_2$, NH(CH$_3$), and N(CH$_3$)$_2$. In some cases, R is independently hydrogen or alkyl.

The term "amido" as used herein refers to —C(O)NH$_2$, —C(O)NR$_2$, —NRC(O)R or —NHC(O)H, where each R is independently hydrogen, optionally substituted alkyl, optionally substituted heteroalkyl, optionally substituted cycloalkyl, optionally substituted heterocycloalkyl, optionally substituted aryl or optionally substituted heteroaryl. In some cases, the amido group is —NHC(O)alkyl or —NHC(O)H. In various cases, the amido group is —C(O)NH(alkyl) or —C(O)NH(substituted alkyl). A non-limiting example of an amido group is —NHC(O)CH$_3$.

As used herein, a substituted group is derived from the unsubstituted parent structure in which there has been an exchange of one or more hydrogen atoms for another atom or group. A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and (B) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected from:

(i) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and (ii) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected from:

(a) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl, and (b) alkyl, heteroalkyl, cycloalkyl, heterocycloalkyl, aryl, amino, amido, carbonyl, thiocarbonyl, alkoxycarbonyl, silyl, sulfonyl, sulfoxyl, alkoxy, aryloxy, and heteroaryl, substituted with at least one substituent selected from —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, unsubstituted alkoxy, unsubstituted aryloxy, trihalomethanesulfonyl, trifluoromethyl.

The term "carboxy" or "carboxyl" used herein refers to —COOH or its deprotonated form —COO⁻. $C_{1-10}$carboxy refers to optionally substituted alkyl or alkenyl groups having a carboxy moiety. Examples include, but are not limited to, —CH$_2$COOH, —CH$_2$CH(COOH)CH$_3$, and —CH$_2$CH$_2$CH$_2$COOH.

In some cases, the substituent group(s) is (are) one or more group(s) individually and independently selected from alkyl, cycloalkyl, aryl, heterocyclyl, heteroaryl, hydroxy, alkoxy, aryloxy, mercapto, alkylthio, arylthio, cyano, halo, carbonyl, thiocarbonyl, alkoxycarbonyl, nitro, silyl, trihalomethanesulfonyl, trifluoromethyl, and amino, including mono and di substituted amino groups, and the protected derivatives thereof.

The protecting groups that can form the protective derivatives of the above substituents are known to those of skill in the art and can be found in references such as Greene and Wuts, *Protective Groups in Organic Synthesis;* 3$^{rd}$ Edition, John Wiley and Sons: New York, 2006. Wherever a substituent is described as "optionally substituted" that substituent can be substituted with the above-described substituents.

Mechanism of Switching in MIMs

Figure 7:
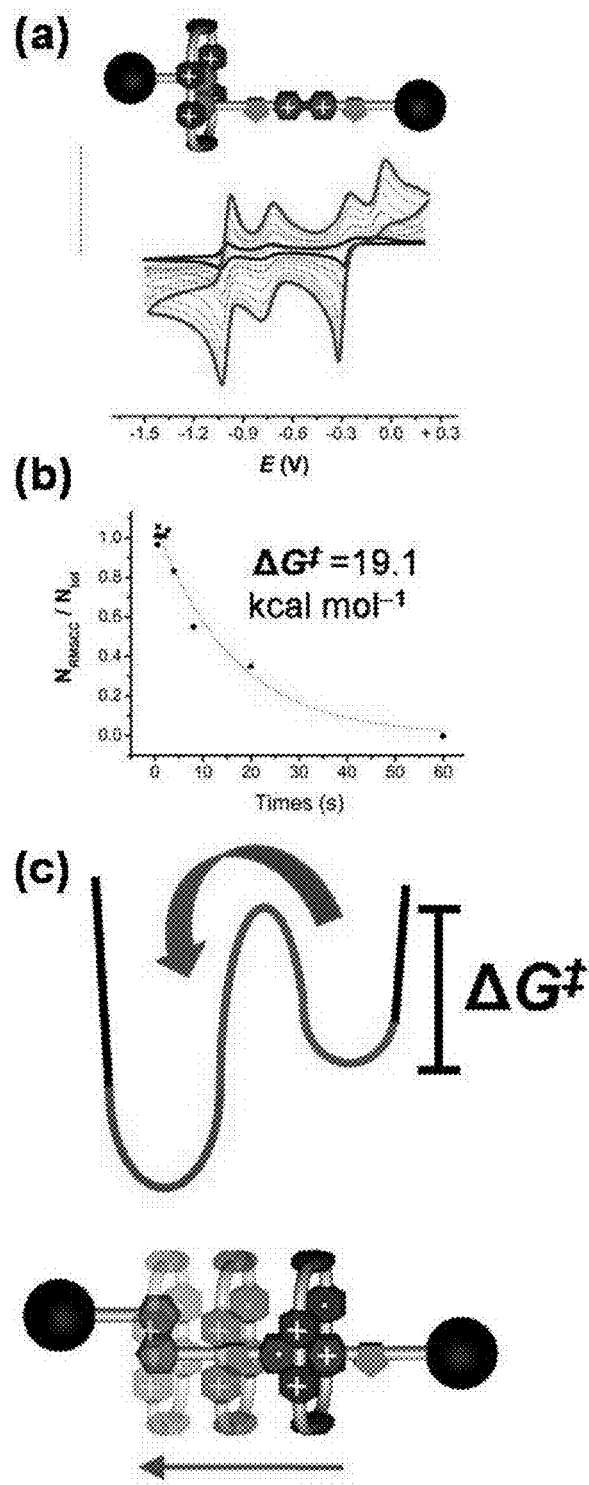
FIG. 7. a) Variable scan rate CV of the DNP-BIPY$^{2+}$ [2]rotaxane R1$^{6+}$. The blue trace was taken at a scan rate of 10 mV s$^{-1}$ leading up to successively higher scan rates up to 500 mV s$^{-1}$, shown as the red trace. The re-oxidation peak at 0 V increases in relative intensity with faster scan rates. b) Quantifying the R-MSCC versus time from the variable scan rate data. Fitting the amount of R-MSCC versus time to a first order decay profile allows for the determination of a barrier to relaxation of 19.1 kcal mol$^{-1}$. c) A thermodynamic landscape constructed from these data for the bisradical oxidation state depicting the relaxation of the R-MSCC to the R-GSCC.

The reduction portion of the CV for the [2]rotaxane R1$^{6+}$ displays similar behavior to the that of the trisradical inclusion complex. Following a three-electron reduction, the diradical dicationic CBPQT$^{2(•+)}$ ring is induced to translate from the 1,5-dioxynaphthalene (DNP) recognition site to encircle the radical cation BIPY$^{+•}$ recognition unit forming the trisradical state as has been previously demonstrated. The re-oxidation of R1$^{6+}$, like the trisradical CBPQT$^{2(•+)}$ ⊂ V$^{•+}$ complex is again scan rate dependent. Similarly, a one-electron oxidation process leading to the formation of the bisradical is observed followed by a two-electron re-oxidation, which can be observed at relatively fast scan rates corresponding to the oxidation of the radically paired bisradical to the fully oxidized state, which likewise immediately leads to the formation of the ground state, where the CBPQT$^{4+}$ ring is encircling the DNP unit. However, in the case of the [2]rotaxane R1$^{6+}$, we observed a difference in the dependence of the second two-electron re-oxidation peak upon changing the scan rate, namely that the presence of the second oxidation peak could be easily observed even at scan rates as slow as 10 mV s$^{-1}$ (FIG. 7). We propose a mechanism that after the one-electron oxidation of the weakly interacting unpaired BIPY$^{+•}$ of the CBPQT$^{2(•+)}$ ring encircling the BIPY$^{•+}$ radical cation of the dumbbell component, this now dicationic BIPY$^{2+}$ of the CBPQT$^{(•+)(2+)}$ ring is now able to recognize the DNP unit through donor-acceptor interactions. Like the pseudorotaxane, the one-electron oxidation causes the formation of a metastable intermediate, the corresponding bisradical, which in the case of the [2]rotaxane R1$^{6+}$, leads to a mechanical movement of the ring in order that it may encircle the DNP as the corresponding R-ground state as consequence of it being the most thermodynamically favorable position due to a combination of favorable donor-acceptor interactions and unfavorable columbic repulsion.

In order to support this mechanism of relaxation from the radically paired bisradical to the unpaired bisradical, we have also synthesized and studied by variable scan rate CV the reduction behavior of a single station [2]rotaxane incorporating only a BIPY$^{2+}$ moiety in the dumbbell component with no other accompanying pi-donor recognition stations. In the case of this [2]rotaxane, we expect that no relaxation would occur, which would result in observing no scan rate dependent behavior in the reduction region of the CV. Indeed, this is the case. The relative intensities of the first and second re-oxidation peaks were scan rate independent (see SI for further discussion).

Although in the case of the [2]rotaxane R1$^{6+}$ "one-half" of the CBPQT$^{(•+)(2+)}$ ring is still able to recognize the BIPY$^{•+}$ radical cation of the dumbbell component, we hypothesize that the presence of the dication in the CBPQT$^{(•+)(2+)}$ ring acts to further lower the stability of the radically paired bisradical translational isomer making the population distribution of the radically spin-paired bisradical essentially zero at thermodynamic equilibrium. Following translation of the CBPQT$^{(•+)(2+)}$ to the DNP moiety, the re-oxidation potentials of the remaining BIPY$^{•+}$ radical cations of the R-GSCC shift to more negative potentials, and so the second two-electron re-oxidation peak is observed to decrease at slower scan rates, just as was the case for the [2]pseudorotaxane CBPQT$^{2(•+)}$ ⊂ V$^{•+}$. Quantifying the amount of radically paired bisradical intermediate as a function of time, we can generate the decay profile shown in FIG. 7b. We propose a first-order relaxation mechanism, in which the rate of relaxation is dependent only on a rate constant and the concentration of the radically paired bisradical. Fitting the data to a first-order decay profile and using the extracted time constant in the Eyring equation reveals the free energy barrier to relaxation $\Delta G^{\ddagger}$ to be 19.1 kcal mol$^{-1}$. From these kinetic data we can construct a thermodynamic profile shown if FIG. 7c governing the relaxation of the radically paired to the unpaired bisradical that occurs after the initial one-electron oxidation.

Use of Reducing Agents to Form Complexes

Zinc dust was activated by stirring with dilute HCl during 10-15 minutes, and then washed several times with distilled water, ethanol, and absolute diethyl ether before rigorous drying. This procedure removes oxides from the surface of zinc, which form slowly upon standing in air. All the studies were carried out with spectroscopic grade acetonitrile (Acros Organics≥99.9% for spectroscopy). All the stock solutions of CPBQT.4PF$_6$ and MV.2PF$_6$ were prepared by weighing using an AG 245 Mettler Toledo analytical balance (precision 0.01 mg) and complete dissolution in MeCN was achieved using an ultrasonic bath (Bandelin Sonorex RK102 Transistor). Their concentrations were thus obtained by weighing the appropriate amounts. Reduction of CPBQT$^{4+}$ and MV$^{2+}$ into the corresponding bisradical CPBQT$^{2+•}$ and monoradical MV$^{+•}$ was achieved under argon (CO$_2$- free and O$_2$-free argon using a Sigma Oxiclear cartridge) in less than one hour by vigorous stirring with activated zinc dust and was monitored using absorption spectrophotometry. After which time, the zinc dust is filtered of using a 0.45 μm syringe filter still inside of the glovebox. The colored solution is then ready to use without further purification.

Other reducing agents can be used, more particularly reducing agents with an oxidation potential that is compatible with the reduction of CPBQT$^{4+}$ and the compound of formula (I) to the tris-radical di-cation complex. In the electrochemical series, metals at the top of the series are good at giving away electrons. They are good reducing agents. The reducing ability of the metal increases as one increases across the series. Therefore, all the metals which are placed above Zinc in the electrochemical series or in other words, metals which posses oxidation potenial higher than Zn (0.76 V) can be used as the reductant. For example Li (3.04 V), K (2.92 V), Ba (2.90 V), Ca (2.76 V), Na (2.71 V), Mg (2.37 V), Al (1.66 V), Mn (1.18 V) can be used as a reductant. The values of standard electrode potentials are given in volts relative to the standard hydrogen electrode. It is important to note, however, that these reducing agents are likely strong enough to reduce the CBPQT$^{4+}$ ring and BIPY$^{2+}$ threads to their neutral states, $CBPQT^0$ and $BIPY^0$, respectively. In order to arrive at the radical cation state, the neutal $CBPQT^0$ and $BIPY^0$ following reduction are combined with a stoichiometric equivalent of $CBPQT^{4+}$ and $BIPY^{2+}$. At this point the neutral $CBPQT^0$ and $BIPY^0$ will undergo electronic dispropotionation with $CBPQT^{4+}$ and $BIPY^{2+}$ resulting in a solution containing only the $CBPQT^{2(\cdot+)}$ and $BIPY^{\cdot+}$ radical cations.

The following is a list of other common reducing agents that could be potentially used to reduce $CBPQT^{4+}$ ring and $BIPY^{2+}$ threads to their neutral states: Nacent hydrogen, sodium amalgam, $NaBH_4$, sulfite salts (e.g. $Na_2S_2O_4$), Zn(Hg) alamgam, oxalic acid, formic acid, ascorbic acid, and coboltocene.

Reducing agents that are less preferred, due to possible side-reactions under many commonly employed conditions, are lithium aluminium hydride (LAH), $SnCl_2$, hydrazine, and, diisobutylaluminium hydride (DIBAL-H).

Crystallization Techniques to Form Crystals of Complexes

Figure 8:
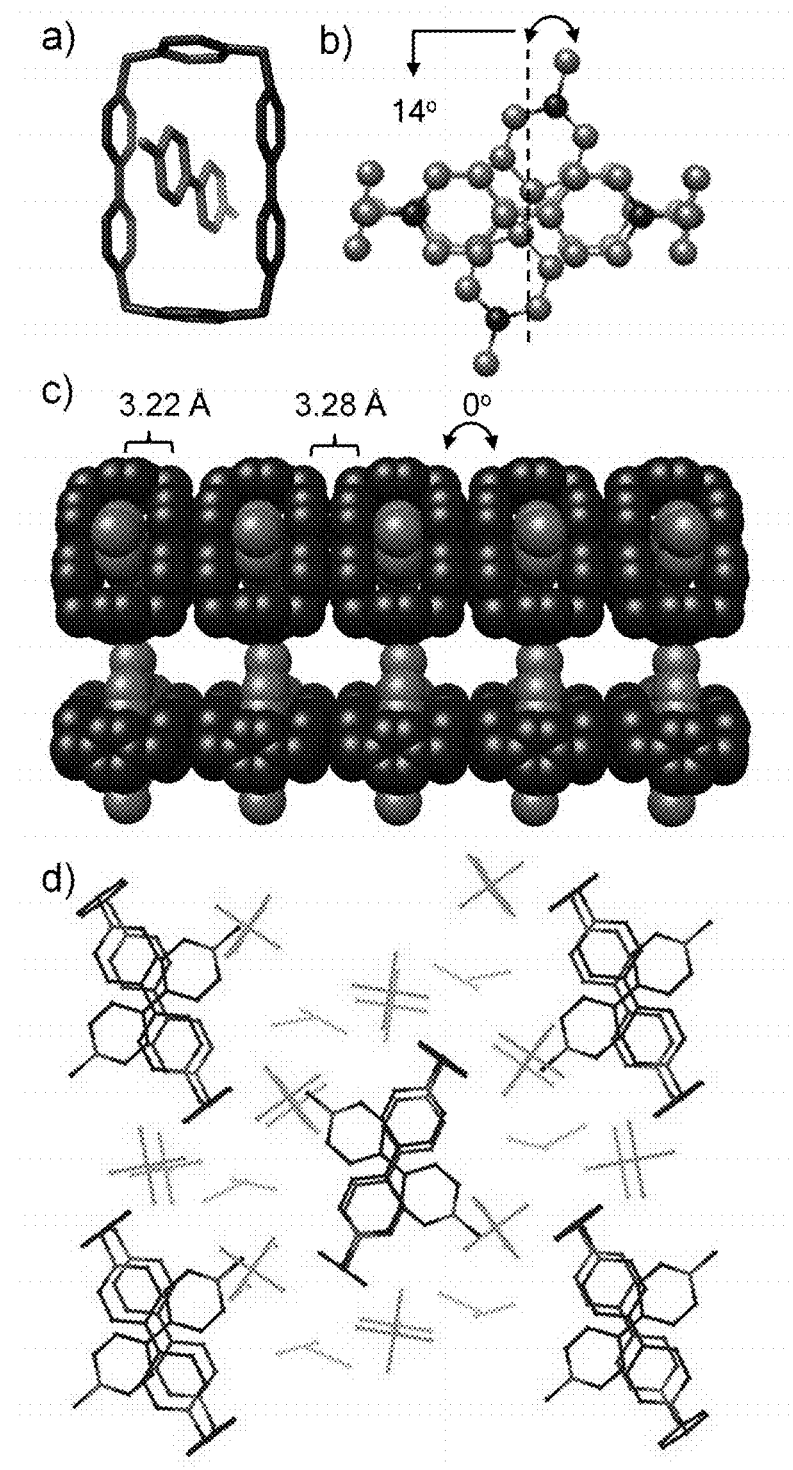
FIG. 8. Solid-state superstructures of the trisradical cation CBPQT$^{2(\bullet+)}$ ⊂ MV$^{\bullet+}$ inclusion complex obtained by single-crystal X-ray crystallography. a) Wireframe representation of the CBPQT$^{2(\bullet+)}$ ⊂ MV$^{\bullet+}$ inclusion complex. b) Ball-and-stick representation of the CBPQT$^{2(\bullet+)}$ ⊂ MV$^{\bullet+}$ inclusion complex from a side-on perspective, illustrating the angle of offset from orthogonality of the MV$^{\bullet+}$ occupying the cavity of the CBPQT$^{2(\bullet+)}$. c) Plan view using a space-filling representation of the long-range packing order of the trisradical tricationic CBPQT$^{2(\bullet+)}$ ⊂ MV$^{\bullet+}$ inclusion complex, which forms a continuous radical-radical π-stack. The PF$_6^-$ counterions, have been omitted for clarity. d) Side-on view showing the relative positions of the PF$_6^-$ counterions.

Single crystals of the $CBPQT^{2(\cdot+)} \subset MV^{\cdot+}$ complex were grown from MeCN using slow-vapor diffusion of $iPr_2O$ under inert conditions, i.e., inside a glovebox, at room temperature. We used zinc dust to affect the reduction of the $CBPQT^{4+}$ and $MV^{2+}$ to their respective radical cation forms. The solid-state structure as determined by X-ray crystallography further supports (FIG. 8) the formation of the trisradical tricationic complex. The inclusion complex was observed to be associated with three hexflurorophosphate counteranions in the solid-state, supporting the hypothesis that each of the $BIPY^{2+}$ units is reduced to its radical cation form. The $MV^{\cdot+}$ is situated inside the cavity of the $CBPQT^{2(\cdot+)}$ ring in a centrosymmetrtic fashion, with 3.22 Å centroid-to-centroid transannular separation from each of the $BIPY^{\cdot+}$ radical cation subunits of the cyclophane, with an 14° angle of offset (FIG. 8) from the plane orthogonal to the one defined by the four N atoms of the ring. We hypothesize this deviation from orthoganility maximizes the amount of π-overlap between $MV^{\cdot+}$ and $CBPQT^{2(\cdot+)}$. No torsional twisting of any of the three $BIPY^{\cdot+}$ units of the complex about their 4,4'-C—C bond is apparent, a phenomenon which is not generally observed for complexes involving the $CBPQT^{4+}$ ring—at least in its fully oxidized form—when bound with electron-rich guests. These structural details are in good agreement with the structure predicted from theoretical calculations reported on previously. The extended superstructure reveals a continuous $BIPY^{\cdot+}$ radical cation π-stack, with adjacent complexes lying in register "shoulder-to-shoulder" 3.28 Å apart from each other.

Figure 9:
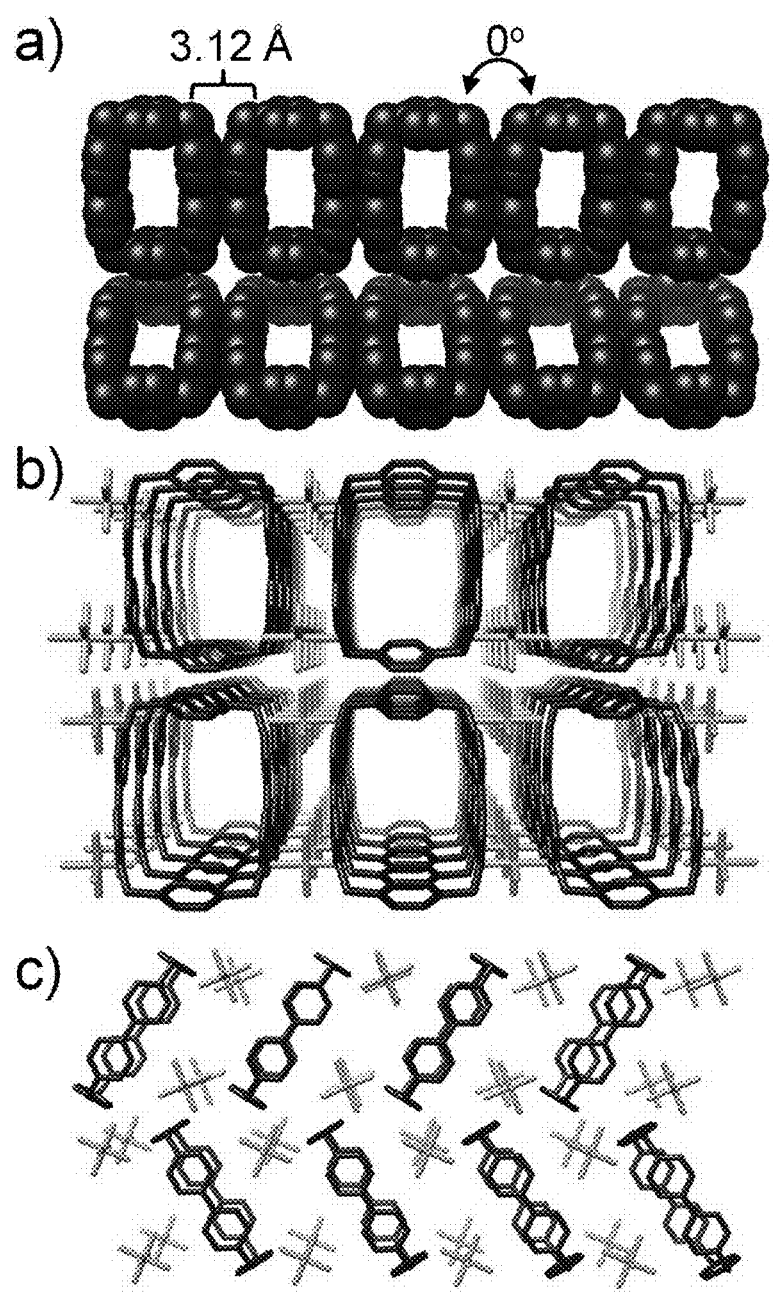
FIG. 9. Solid-state superstructure of the diradical dication CBPQT$^{2(\bullet+)}$ ring obtained by single crystal X-ray crystallography. a) In common with the trisradical CBPQT$^{2(\bullet+)}$ ⊂ MV$^{\bullet+}$ inclusion complex, the CBPQT$^{2(\bullet+)}$ solid-state superstructure reveals a CBPQT$^{2(\bullet+)}$ rings of radical cation-radical cation along the a crystallographic axis interactions between its BIPY$^{\bullet+}$ constituent subunits. The counterions, PF$_6^-$ have been omitted for clarity. b) A wireframe representation (plan view) of the solid-state superstructure of CBPQT$^{2(\cdot+)}$, depicting the porous channels formed by the unoccupied interiors diradical dicationic rings.

As a control, we investigated the crystal growth of the $CBPQT^{2(\cdot+)}$ alone in solution. Crystals were readily obtained from slow-vapor diffusion of $iPr_2O$ in a solution of $CBPQT^{2(\cdot+)}$ in MeCN. Remarkably, long dark, opaque needle-like crystals up to an inch in length were observed after less than a week of crystal growth. Single crystal X-ray crystallographic analyses revealed (FIG. 9) first of all that the ring crystallized from solution into the solid-state as the diradical dication $CBPQT^{2(\cdot+)}$ as can be reckoned from the $PF_6^-$ counteranion count. No torsional twist was again observed in the $BIPY^{\cdot+}$ units of the $CBPQT^{2(\cdot+)}$ ring, an observation which is consistent with that observed for the trisradical complex. The centroid-to-centroid transannular distance spanning the length between the two $BIPY^{\cdot+}$ units of the ring is 6.92 Å, a remarkably longer distance compared to the trisradical complex, whose analogous distance is 6.43 Å. These observations indicate that the $CBPQT^{2(\cdot+)}$ ring is able to flex in order to accommodate the $MV^{\cdot+}$ guest in such a way that reduces the bowing of the $BIPY^{\cdot+}$ units of the ring. As a further consequence to this, the centroid-to-centroid transannular separation between the phenylene units observed in the X-ray structure of the $CBPQT^{2(\cdot+)}$ ring is 10.21 Å, while the analogous distance for the trisradical complex is 10.34 Å. The decreased degree of bowing of the $BIPY^{\cdot+}$ units brought about by inclusion of $MV^{\cdot+}$ serves to increase the distance between the phenylene units of the ring. The superstructure, much like the way the trisradical complex packs in the solid-state, reveals a continuous stack of $CBPQT^{2(\cdot+)}$ rings spaced 3.12 Å apart arranged shoulder-to-shoulder with a zero degree angle of offset—although with void spaces arising from the unoccupied cavities of the rings! In fact, the cavities of the rings arrange in such a way as to form continuous porous channels that run the length of the crystal, with the $PF_6^-$ counterions occupying the space between the rings. Overall, the superstructure is consistent with our understanding of the nature of $BIPY^{\cdot+}$ radical-radical interactions, which serve to "stitch" the $CBPQT^{2(\cdot+)}$ rings together into continuous stacks.

It is possible by varying the substitution of the viologen radical cation thread in the 4,4' positions, using either alkyl-based or aryl-based functionalities, the electronic, UV/Vis spectroscopic and steric properties of the resulting trisradical complexes can be modified, and hence the solid-state properties can be tuned.

Crystallization of Surfaces and Analysis with Scanning Electron Microscopy

Figure 15:
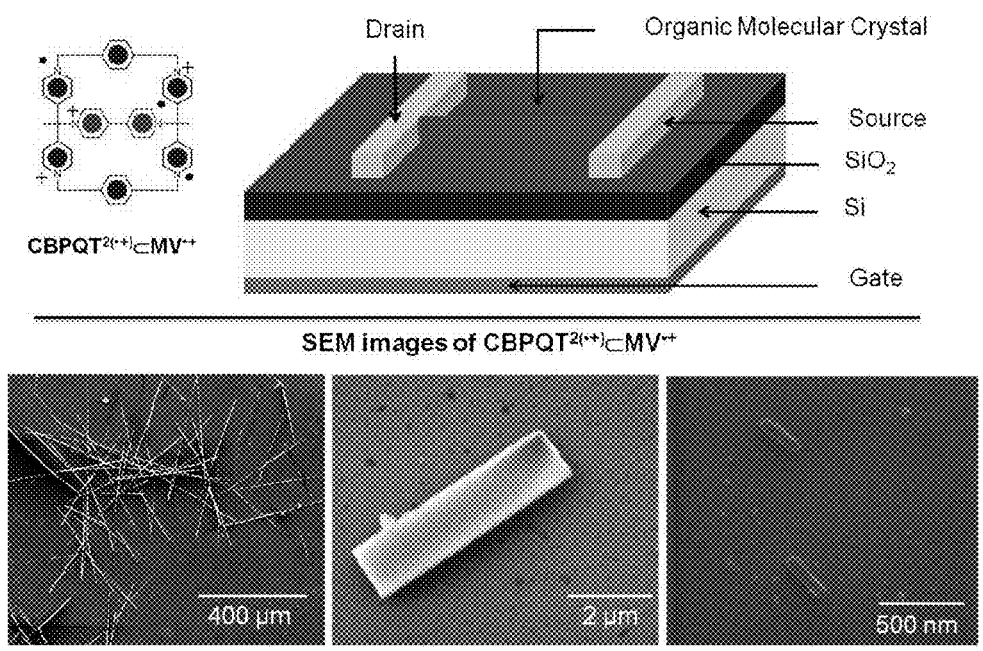
FIG. 15. Diagram of the Organic Field Effect Transistor (OFET) used to study the conductivity of the nanowire crystals of CBPQT$^{2(\cdot+)} \subset$ MV$^{\cdot+}$. Conductivity of a single crystal is measured as a function of the gate voltage. Such measurements allow for the determination of n- or p-type semiconductor characteristics.
Figure 16:
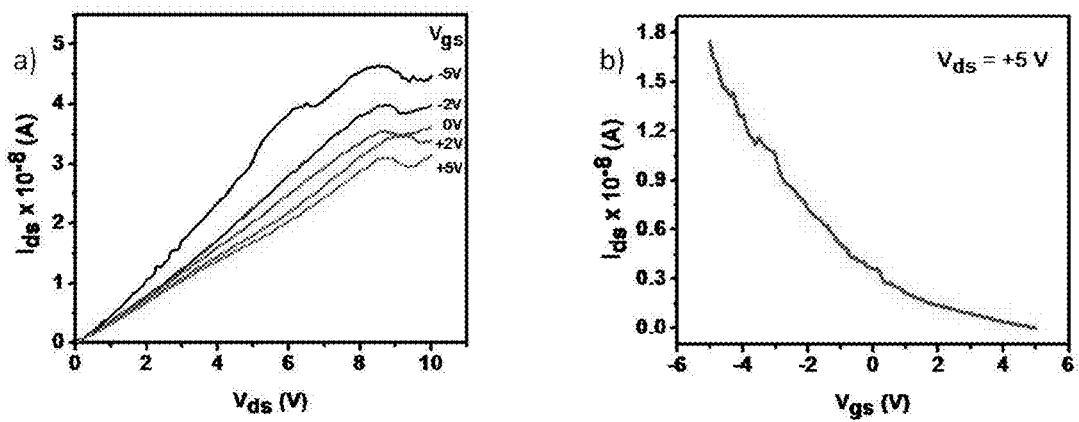
FIG. 16. Field effect transistor characteristics of the OFET composed of single crystals of CBPQT$^{2(\cdot+)} \subset$ MV$^{\cdot+}$ crystals grown on a SiO$_2$/Si substrate: a) output characteristic of the OFET device and b) transfer characteristics of the OFET device, showing p-type semiconductor behavior.
Figure 17:
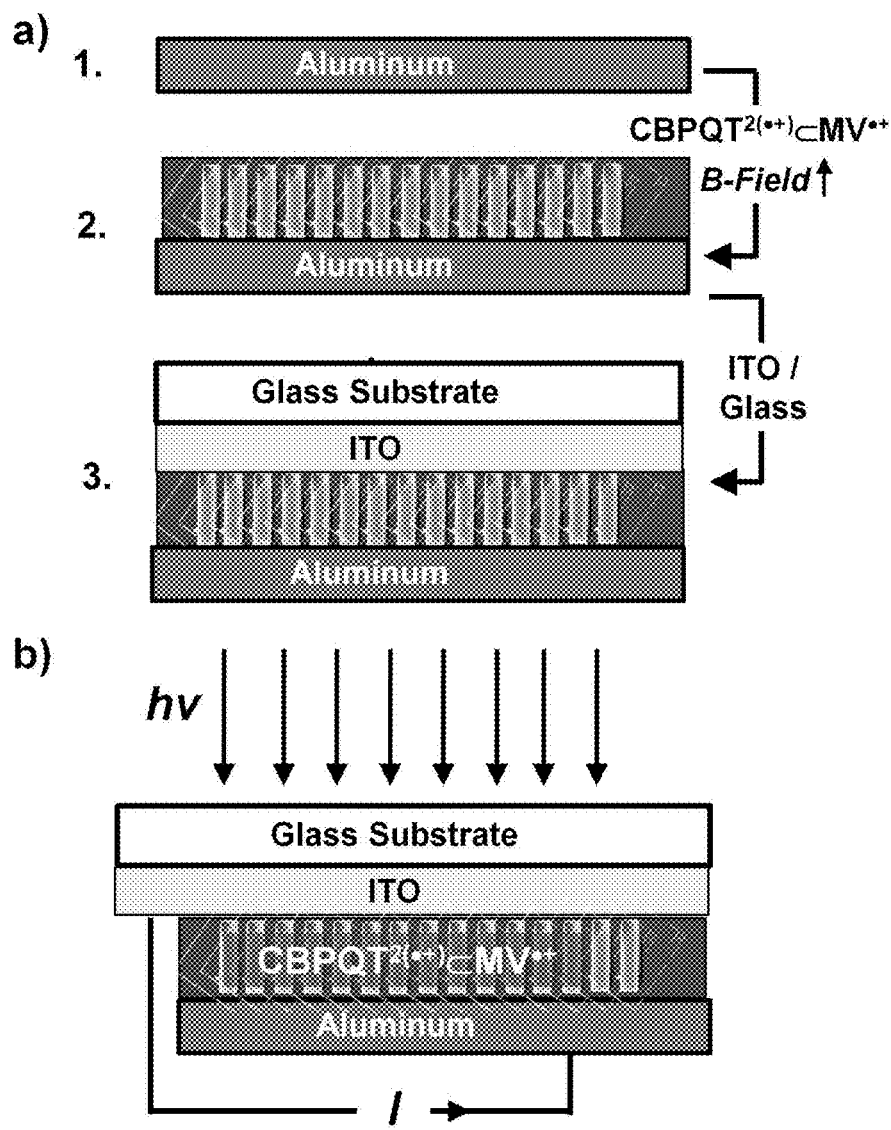
FIG. 17. Proposed single-layer organic solar cell (SLOSC) employing single crystals of CBPQT$^{2(\cdot+)} \subset$ MV$^{\cdot+}$ as the photoactive component. a) Construction of the devices begins with a layer of (1.) aluminum serving as the hole-collecting electrode. Growth of the CBPQT$^{2(\cdot+)} \subset$ MV$^{\cdot+}$ crystals in the presence of a magnetic field (B) is expected (2.) to result in crystals all aligned in a similar direction. Deposition of a layer of indium tin oxide (ITO) as the electron-collecting electrode (3.) and a protecting glass substrate completes the construction of the device. b) Upon irradiation of light, a photocurrent is expected to result. The high level of order in the device is excepted to result in efficient excitation separation leading to high efficiency.
Figure 18:
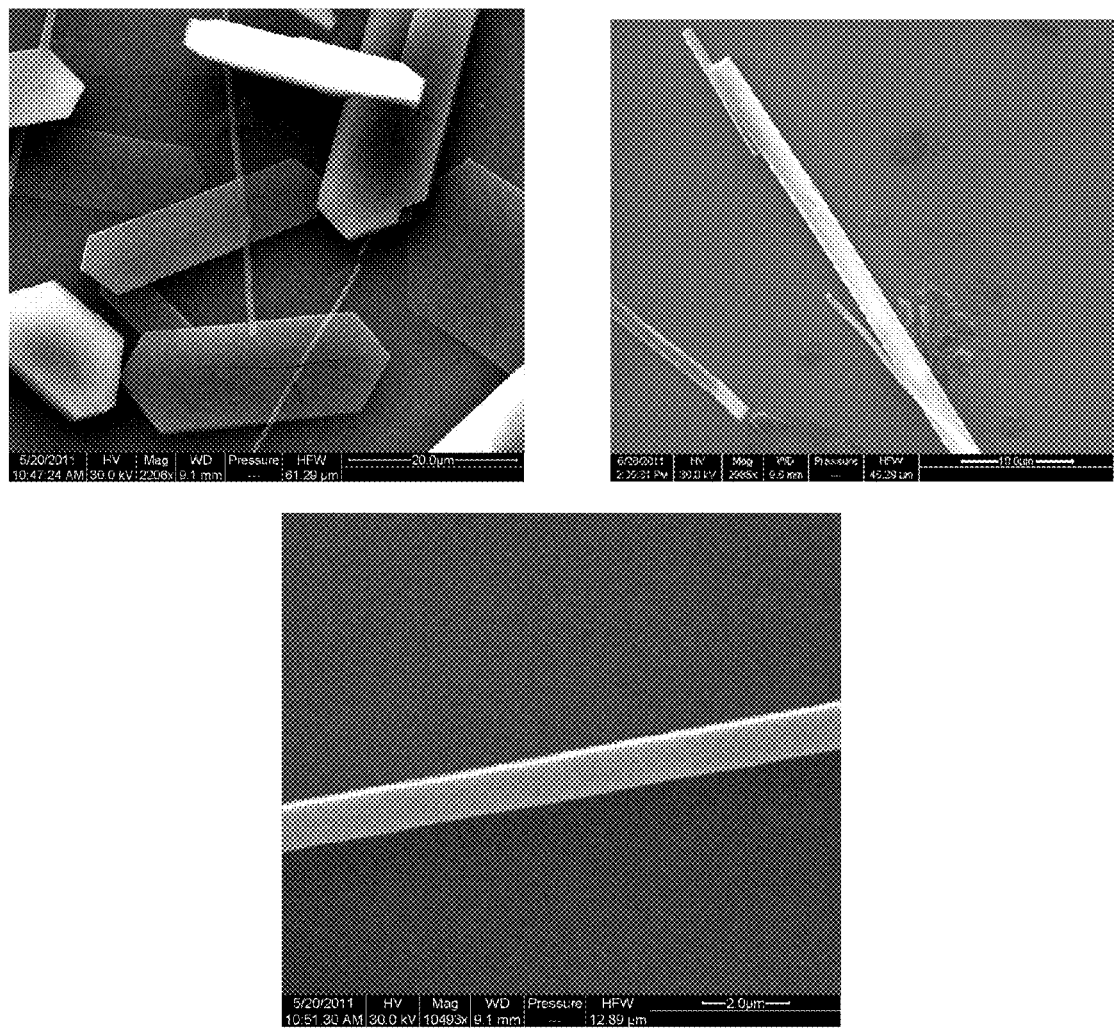
FIG. 18 shows three examples of nanowires formed from crystal complexes disclosed herein.

Crystallization of the trisradical trication inclusion complex $CBPQT^{2(\cdot+)} \subset MV^{\cdot+}$ can be made to occur on silicon surfaces using reduction with Zn dust and slow-vapour diffusion methodologies previously described. Analysis with Scanning Electron Microscopy (SEM) reveals that these crystals form long molecular wires several micrometers long. The length of the crystal wires can be controlled by varying the concentration of the solution of $CBPQT^{2(\cdot+)} \subset MV^{\cdot+}$ prior to slow-vapor diffusion. In particular, larger concentrations lead to larger crystals. Visual inspection of crystals grown large enough to be seen by the naked eye reveals that the crystals are black, that is, they strongly absorb wavelengths across the visible spectrum. These crystals have been incorporated into a field effect transistor (FET) device (FIG. 15) in order to determine their conductivity. These experiments reveal that the crystals are conductive (FIG. 16) and act as p-type semiconductors. The fact that these crystals are conductive and strongly absorb light in the visible region renders them with considerable potential to serve as the active organic component in either single-layer organic solar cells (SLOSCs). SLOSCs have fallen out of favor as a consequence of their exactions tendency to recombine before they are able to be collected at their respective electrodes. This is likely a result of the low long-range order of the organic material being employed, usually a conjugated polymer. We propose to construct (FIG. 17) SLOSCs with these crystals by the following methodology. First of all, we have shown by EPR that the trisradical $CBPQT^{2(\cdot+)} \subset MV^{\cdot+}$ complex is paramagnetic in solution. Therefore, application of a magnetic field (B) during crystal growth is likely to result in growth of the crystal along a direction a vector dictated by the direction of the applied magnetic field. In this way, we expect to be able to grow a layer of crystals all aligned in a similar direction. Performing this procedure on an aluminum surface acting as the bottom electrode is expected to result in an ordered array of crystals (FIG. 17a). Following this, a layer of indium tin oxide (ITO) and glass on top of the crystals will serve as the other electrode. Upon irradiation with light (FIG. 17b), a photocurrent is expected to result with electrons flowing to the ITO layer and holes propagating to the aluminum layer. Since SLOSC are intrinsically simpler by design than the currently favored double-layer donor-acceptor organic solar cells, the design proposed herein will offer a considerable advantage. Examples of crystal nanowires are shown in FIG. 18.

Characterization by Isothermal Titration Calorimetry and UV/Vis Spectroscopy

Figure 10:
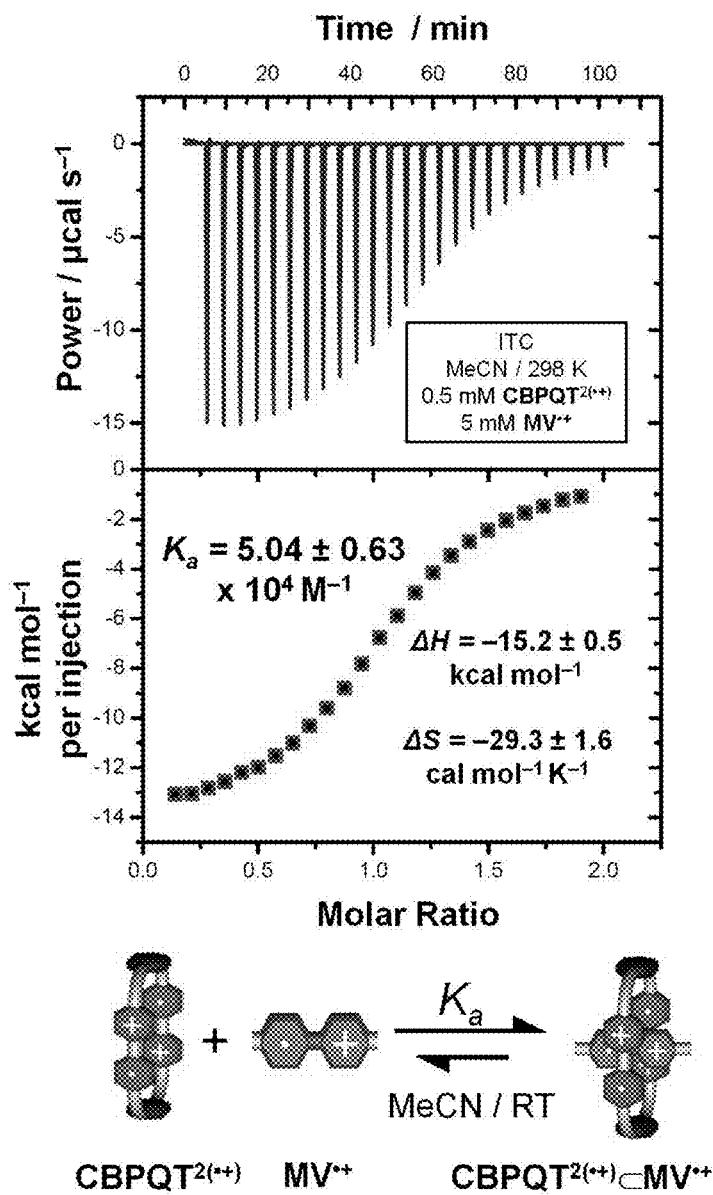
FIG. 10. The isothermal titration calorimetry (ITC) traces obtained when measuring the thermodynamic parameters ($K_a$, $\Delta H$, $\Delta S$) governing the formation of the trisradical CBPQT$^{2(\cdot+)} \subset$ MV$^{\cdot+}$ inclusion complex. All the ITC experiments were performed in MeCN at 298 K. The values for $K_a$, $\Delta H$ and $\Delta S$ reported above are averages over four runs, and the errors are the associated standard deviations from these four runs.

We were able to obtain thermodynamic parameters governing the stability of the trisradical complex by performing ITC experiments at room temperature in MeCN under the inert conditions provided by a glove box. Solutions of $CBPQT^{2(\cdot+)}$ and $MV^{\cdot+}$ were prepared individually using zinc dust as the reducing agent. Results (FIG. 10) from ITC confirm the 1:1 stoichiometry of the complex and reveal an association constant $(K_a)$ value of $5.04\pm0.63\times10^4$ $M^{-1}$. As expected, the binding is enthalpically driven with a $\Delta H$ value of $-15.2\pm0.5$ kcal $mol^{-1}$ with an entropic cost of $-29.3\pm1.6$ cal $mol^{-1}$ $K^{-1}$ for $\Delta S$.

Figure 11:
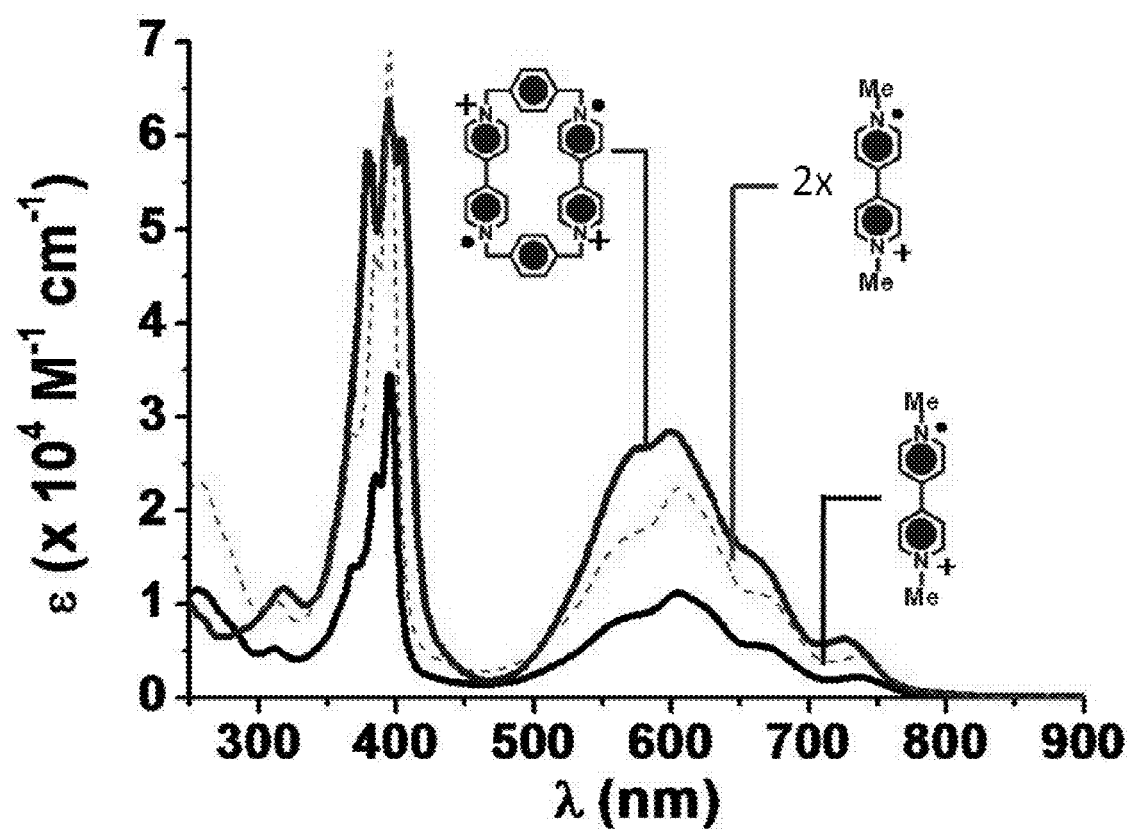
FIG. 11. Electronic spectra of CBPQT$^{2(\cdot+)}$ and MV$^{\cdot+}$. Comparison of the electronic spectrum of CBPQT$^{2(\cdot+)}$ with the sum of the electronic spectra of two MV$^{\cdot+}$ indicates significant differences in agreement with strong electronic coupling in the ground state between the two chromophores. Solvent: MeCN; T=25.0(2)° C.

The absorption spectra of the radical cation $MV^{+\cdot}$ and of the diradical dication $CPBQT^{2(\cdot+)}$ were first of all recorded alone in solution at concentrations of $\sim5\times10^{-5}-10^{-4}$ M to verify the absence of intermolecular radical-radical interactions between like species under the experimental conditions employed. The absorption spectra of $MV^{+\cdot}$ and of $CPBQT^{2(\cdot+)}$ are both characterized (FIG. 11) by two sets of finely-structured absorptions (vibronic coupling) centered on $\sim390$ nm and 600 nm, respectively. No absorption was observed in the near IR region, an observation which substantiates the absence of intermolecular radical-radical interactions—namely, dimerization—in MeCN. The electronic spectrum of $CPBQT^{2(\cdot+)}$ was compared to the sum of the electronic spectra of two stoichiometric equivalents of $MV^{+\cdot}$ in order to investigate the ability of the two $BIPY^{\cdot+}$ units in $CPBQT^{2(\cdot+)}$ to interact in a noncovalent fashion. The larger extinction coefficients of the $CPBQT^{2(\cdot+)}$ diradical dication compared to the sum of two $MV^{+\cdot}$ radical cations, suggests an intramolecular dipole-dipole interaction in the ground state between the $CPBQT^{2(\cdot+)}$ ring's two $BIPY^{\cdot+}$ radical cation units, which are held rigidly apart at a distance of approximately 7 Å within the $CPBQT^{2(\cdot+)}$ diradical diaction. This observation is in good agreement with EPR results previously obtained, data of which supports the hypothesis of intramolecular dipole-dipole interactions.

Figure 12:
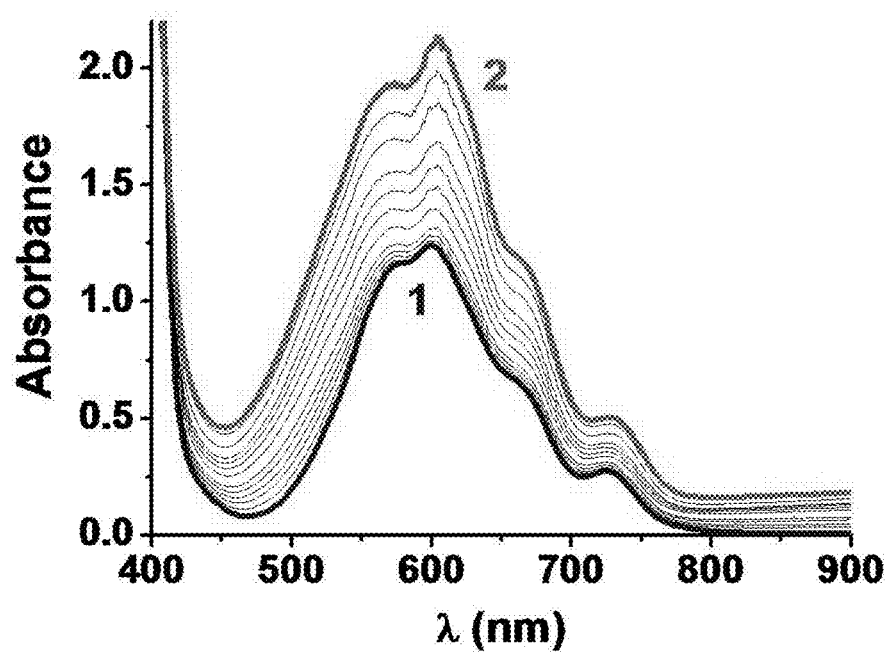
FIG. 12. UV/Vis Absorption spectrophotometric titration of CBPQT$^{2(\cdot+)}$ by MV$^{\cdot+}$. Solvent: MeCN; T=25.0(2)° C.; Reducing agent: activated Zn dust; l=1 cm. (1) [CBPQT$^{2+}$]$_0$=4.36×10$^{-5}$ M; (2) [MV$^{+\cdot}$]$_0$/[CBPQT$^{2+\cdot}$]$_0$=4.38.

The strength of the association between the $CPBQT^{2(\cdot+)}$ and the $MV^{\cdot+}$ was probed in MeCN using UV/Vis absorption spectrophotometry which allowed us to assess the spectroscopic and thermodynamic parameters associated with the formation of the $CPBQT^{2(\cdot+)} \subset MV^{\cdot+}$ trisradical trication. The recognition of $MV^{\cdot+}$ by $CPBQT^{2(\cdot+)}$ occurs with a significant broadening of the absorption band centered at ca. 604 nm, resulting effectively in the observation of a new band appearing (FIG. 12) around 550 nm, and in the formation of an intense absorption band straddling 1075 nm. The processing of these spectrophotometric data allowed for a further determination of the stability constant $(K_a)$ for the trisradical trication inclusion complex, in addition to affording the corresponding electronic spectrum. The electronic spectrum of the 1:1 trisradical tricationic $CPBQT^{2(\cdot+)} \subset MV^{\cdot+}$ complex displays the characteristic spectroscopic features of $BIPY^{\cdot+}$ radical-radical interactions (pimerization)—namely a broad NIR band as well as an increase in intensity in the 500-600 nm region when referenced to the free components alone in solution. The results from this titration reveal that the $K_a$ value is $7.9\pm5.5\times10^4 M^{-1}$, an association constant which is consistent within experimental error of the binding constant determined from ITC experiments. Table 1 summarizes the thermodynamic parameters obtained from the ITC and UV/Vis spectroscopic data.

Mechanism of Mechanical Bond Formation by Threading-Followed-by-Stoppering

Figure 13:
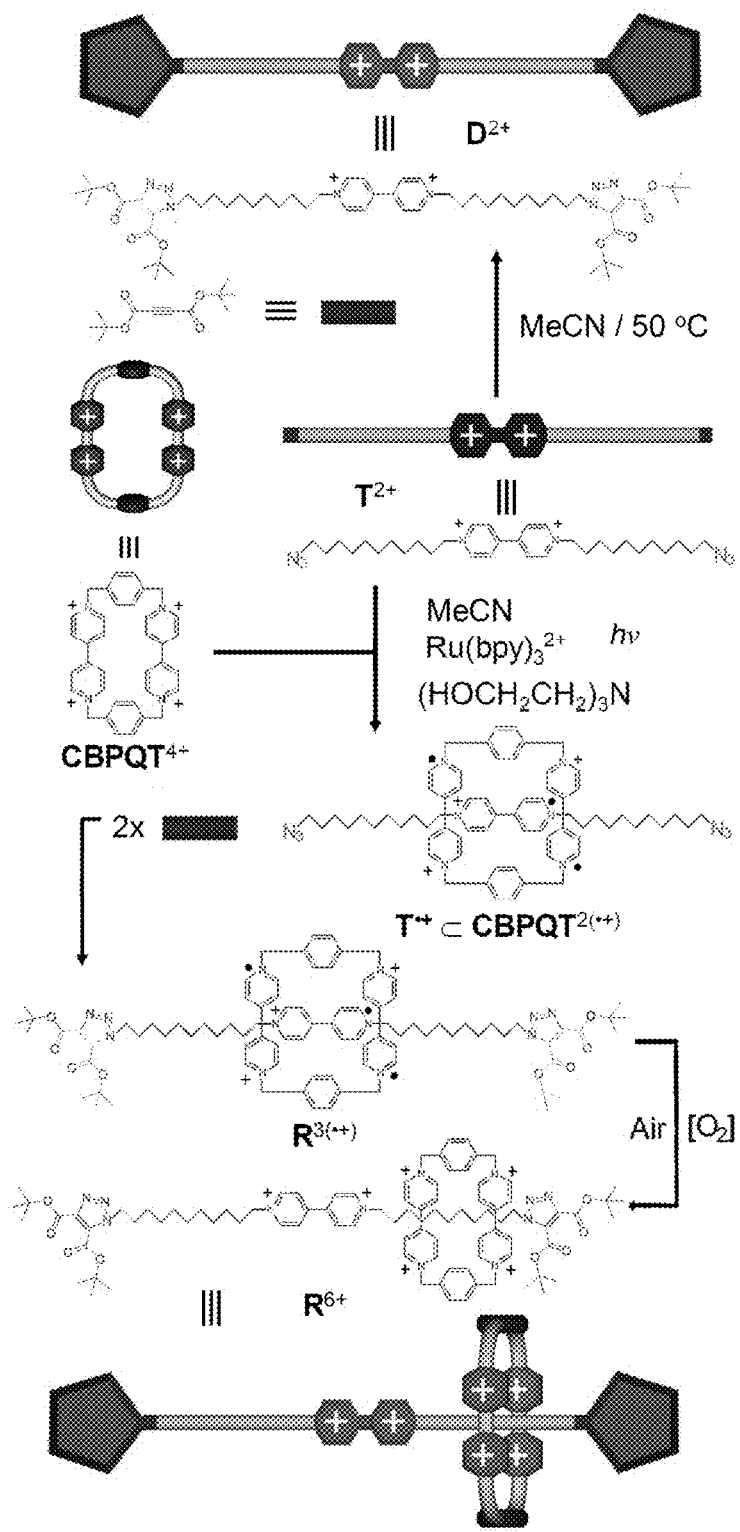
FIG. 13. The radically promoted, template-directed synthesis of the [2]rotaxane R·6PF$_6$ via the intermediacy of the highly stable [2]pseudorotaxane [T$^{\cdot+} \subset$ CBPQT$^{2(\cdot+)}$] which affords the [2]rotaxane R$^{3(\cdot+)}$, prior to its subsequent aerial oxidation to give R·6PF$_6$ during its purification and isolation. The PF$_6^-$ counterions are omitted for the sake of clarity. The graphical representations of the structural formulas have been introduced to aid and abet the presentations of molecular structures in FIGS. 2-4.

The successful template-directed synthetic strategy for the assembly of the [2]rotaxane $R \cdot 6PF_6$ is illustrated in FIG. 13. The viologen derivative $T^{2+}$ with two terminal azide functions was prepared in high overall yield in three steps from 11-bromo-1-undecanol and 4,4'-bipyridine. The template-directed synthesis of the [2]rotaxane $R \cdot 6PF_6$ was achieved using a copper free azide-alkyne 1,3-dipolar cycloaddition after the $BIPY^{2+}$ dications in both $CBPQT^{4+}$ and $T^{2+}$ had been reduced to $BIPY^{\cdot+}$ radical cations to promote the formation of the $T^{\cdot+} \subset CBPQT^{2(\cdot+)}$ inclusion complex. In order to effect the reduction of all three $BIPY^{2+}$ units simultaneously to their respective radical cations in both $T^{\cdot+}$ and $CBPQT^{2(\cdot+)}$, the well known $[Ru(bpy)_3]^{2+}$ reducing system which can be activated by visible light, was chosen because of its highly efficient reduction of $BIPY^{2+}$ units using photo-induced charge-transfer. Triethanolamine, which was employed as the sacrificial electron donor, prevents back electron transfer from the $BIPY^{\cdot+}$ radical cation to the $[Ru(bpy)_3]^{3+}$ species. In order to complete the template-directed synthesis of the [2]rotaxane by a threading-followed-by-stoppering strategy, a 1,3-dipolar cycloaddition between di-tert-butyl acetylenedicarboxylate—the precursor to the two stoppers—and the terminal azide groups on the thread component of the inclusion complex was performed. The [2]rotaxane $R \cdot 6PF_6$ was isolated in 35% yield after a work-up during which time all the $BIPY^{\cdot+}$ radical cations were oxidized back to $BIPY^{2+}$ dications by atmospheric oxygen.

Mechanism of Mechanical Bond Formation by Clipping

Figure 14:
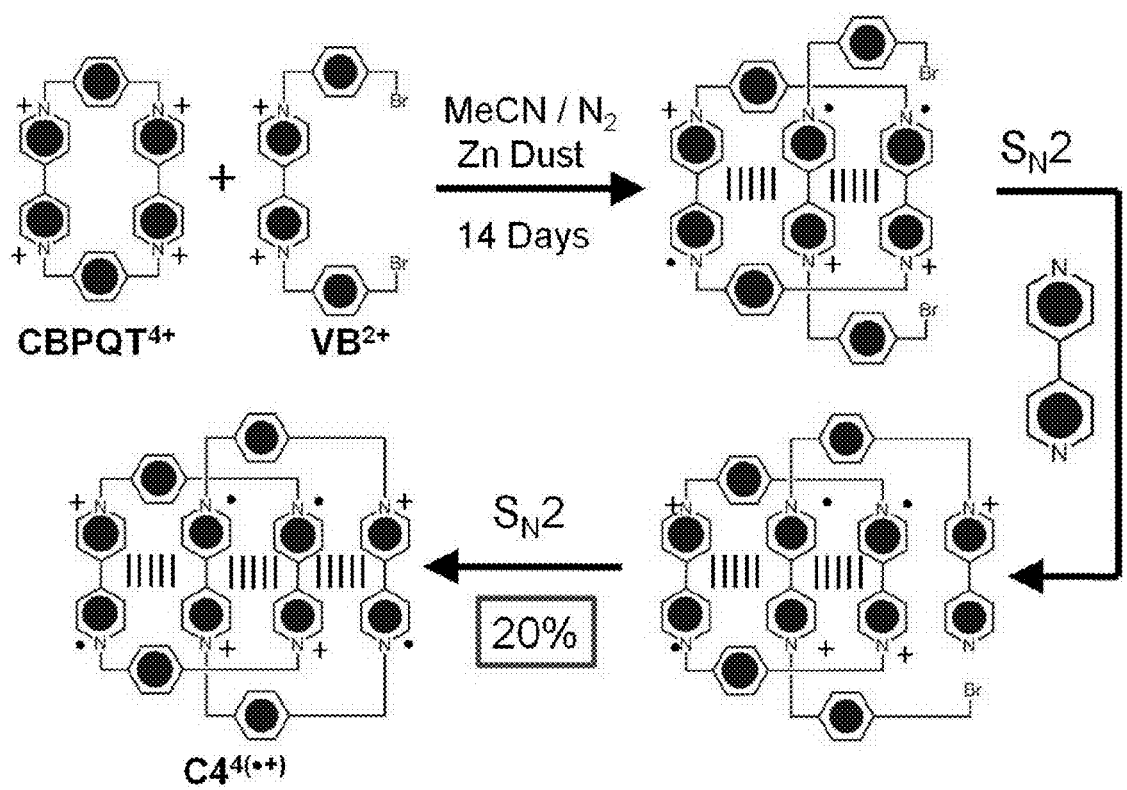
FIG. 14. Template-directed synthesis of the homo[2]catenane C$^{4(\cdot+)}$ employing a clipping strategy relying on BIPY$^{\cdot+}$ radical-radical interactions. The synthesis begins with a 1:1 mixture of CBPQT$^{4+}$ and VB$^{2+}$ in MeCN. The solution is exposed to zinc dust in order to bring about reduction of the components to their radical cation forms and induce complexation. The zinc dust is then filtered off and 4,4'-bipyridine is added to the solution. A trisradical intermediate complex undergoes cyclization to afford the final interlocked product.

The successful template-directed strategy employing a clipping mechanism in order to synthesize the homo[2] catenane $C^{4+}$ is shown in FIG. 14. The synthesis begins with a 1:1 mixture of the $CBPQT^{4+}$ ring and the benzyl bromide viologen derivative $VB^{2+}$ in degassed MeCN under an inert atmosphere (glove box). To this solution is added an excess of Zn dust in order to affect the reduction of the two components to their radical cation forms and induce their complexation. The Zn dust is then filtered off, and to the solution is added an equivalent of 4,4'-bipyridine. We propose the reaction proceeds through an oligomeric intermediate prior to cyclization forming the final interlocked product. After purification, the homo[2]catenane is isolated in 20% yield.

EXAMPLES

Example 1

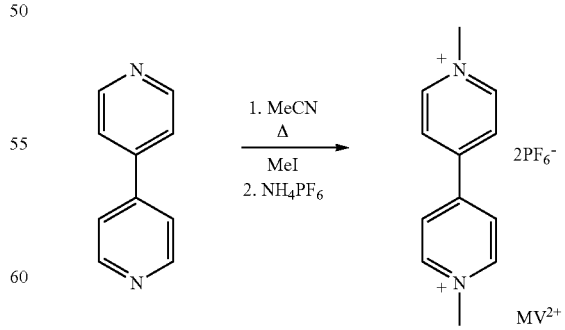

$MV \cdot 2PF_6$: To a solution of 4,4'-bipyridine (1 g, 6.4 mmol) in MeCN (50 mL) was added MeI (2.7 g, 19.2 mmol). The reaction was allowed to stir for two days under reflux, during which time a precipitate was formed. The solvent was reduced to a minimal volume, and to it was added a solution (50 mL) of aqueous NH$_4$PF$_6$. The resulting precipitate was collected by filtration and washed with H$_2$O and ether. The resulting yellow solid was found to be the target product in pure form. Collected 3.0 g (98%).

Example 2

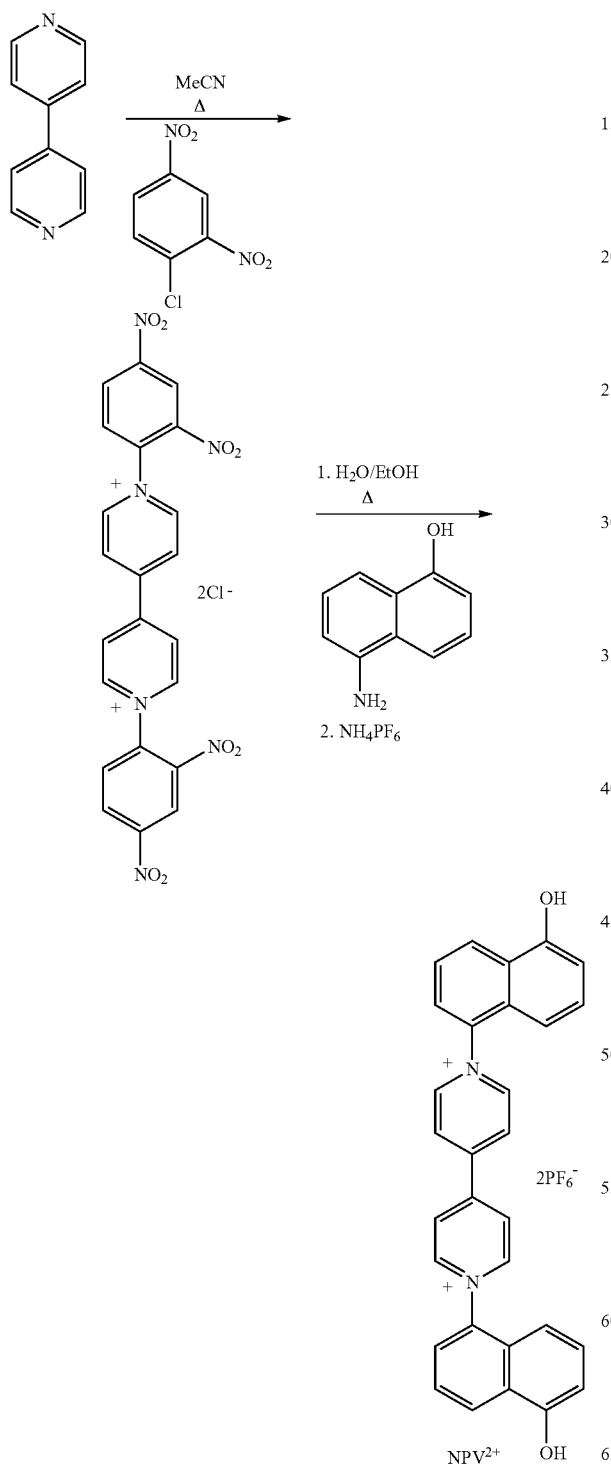

NPV•2PF$_6$: To a solution of 4,4'-bipyridine (1 g, 6.4 mmol) in MeCN (50 mL) was added 1-chloro-2,4-dinitrobenzene (3.9 g, 19.2 mmol). The reaction was set to reflux for 3 d, during which time a precipitate was observed to form. At the end of 3 d, the reaction was allowed to cool to room temperature, and the precipitate was collected by filtration and washed with additional MeCN (25 mL). The solid was allowed to dry under vacuum before being dissolved in a 30:70 mixture of EtOH/H$_2$O also dissolved with 1-amino-5-hydroxynaphthalene (3.1 g, 19.2 mmol). The reaction mixture was set to reflux for 5 d. At the end of this time, the reaction was allowed to cool and the precipitate was removed by filtration. The filtrate was reduced to a minimal volume and to it was added an aqueous solution of NH$_4$PF$_6$. The resulting precipitate was collected by filtration and washed with H$_2$O and ether. Collected an orange solid which was the target product in pure form. Collected 2.8 g (60%).

Example 3

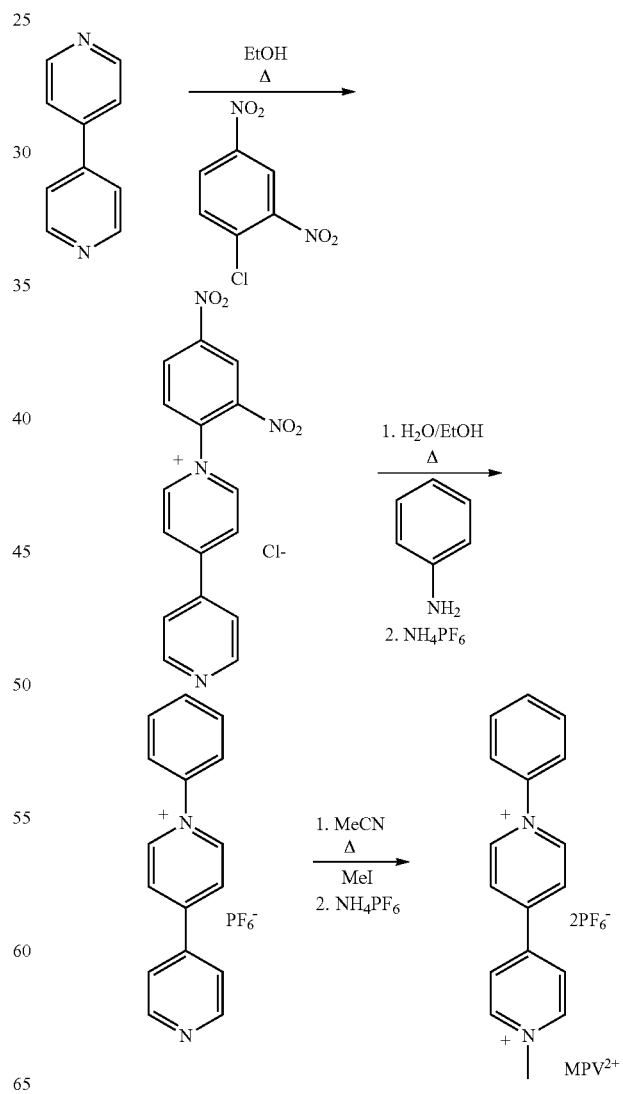

MPV·2PF$_6$: To a solution of 4,4'-bipyridine (2 g, 12.8 mmol) in EtOH (50 mL) was added 1-chloro-2,4-dinitrobenzene (1.3 g, 6.4 mmol). The reaction was allowed to stir under reflux for 2 d. After this time, the reaction was allowed to cool to room temperature and an excess of ether (250 mL) was added to the solution. The resulting precipitate was collected by filtration and dried under vacuum. The dried solid was dissolved in a 70:30 EtOH/H$_2$O mixture along with aniline (1.3 g, 12.8 mmol). The reaction mixture was heated to reflux for 3 d. After this time, the reaction was allowed to cool to room temperature, and the precipitate was removed by filtration. The filtrate was reduced to a minimal volume and to it was added an aqueous solution of NH$_4$PF$_6$. The resulting precipitate was collected by filtration and washed with H$_2$O and dried under vacuum. The dried solid was dissolved in MeCN (50 mL) along with MeI (1.8 g, 12.8 mmol) and the reaction was set to reflux for 2 d. The solvent was reduced to a minimal volume and to it was added an aqueous solution of NH$_4$PF$_6$. The resulting precipitate was collected by filtration and washed with H$_2$O and ether. Collected 2.1 g (60%) of a yellow solid which was the target product in pure form.

Example 4

MPV·2PF$_6$: To a solution of 4,4'-bipyridine (2 g, 12.8 mmol) in EtOH (50 mL) was added 1-chloro-2,4-dinitrobenzene (1.3 g, 6.4 mmol). The reaction was allowed to stir under reflux for 2 d. After this time, the reaction was allowed to cool to room temperature and an excess of ether (250 mL) was added to the solution. The resulting precipitate was collected by filtration and dried under vacuum. The dried solid was dissolved in a 70:30 EtOH/H$_2$O mixture along with aniline (1.3 g, 12.8 mmol). The reaction mixture was heated to reflux for 3 d. After this time, the reaction was allowed to cool to room temperature, and the precipitate was removed by filtration. The filtrate was reduced to a minimal volume and to it was added an aqueous solution of NH$_4$PF$_6$. The resulting precipitate was collected by filtration and washed with H$_2$O and dried under vacuum. The dried solid was dissolved in MeCN (50 mL) along with MeI (1.8 g, 12.8 mmol) and the reaction was set to reflux for 2 d. The solvent was reduced to a minimal volume and to it was added an aqueous solution of NH$_4$PF$_6$. The resulting precipitate was collected by filtration and washed with H$_2$O and ether. Collected 2.1 g (60%) of a yellow solid which was the target product in pure form.

Example 5

R·6PF$_6$: T·2PF$_6$ (167 mg, 0.2 mmol), CBPQT·4PF$_6$ (110 mg, 0.1 mmol), and tris(2,2'-bipyridine)dichlororuthenium (II) hexahydrate (74.8 mg, 0.1 mmol) were dissolved in MeCN (20 mL). The mixture was purged with Ar whilst stirring for 30 min, and then triethanolamine (1.49 g, 10 mmol) and di-tert-butyl acetylenedicarboxylate (226 mg, 1 mmol) were added. The reaction mixture was stirred under an Ar atmosphere in visible light for 3 days. The solvent was evaporated off and the residue was purified by column chromatography (SiO$_2$: MeOH and then 0.1% NH$_4$PF$_6$ in Me$_2$CO). Yellow fractions were collected, concentrated to a minimum volume, from which the product was precipitated on addition of H$_2$O, before being collected by filtration to afford R·6PF$_6$ (80 mg, 35%) as a light-yellow powder.

What is claimed:

1. A complex comprising (a) CBPQT$^{2(·+)}$ and (b) a compound of formula (I):

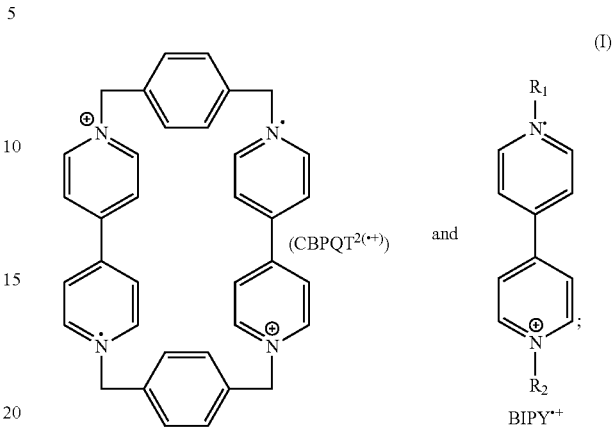

wherein the complex has a 3$^+$ charge and is a tris-radical, and

R$^1$ and R$^2$ are each independently selected from the group consisting of alkyl, cycloalkyl, heterocycloalkyl, aryl, heteroaryl, alkenyl, alkynyl, alkyleneazido, alkylenecycloalkyl, alkyleneheterocycloalkyl, and alkylenearyl, or a salt thereof.

2. The complex of claim 1, wherein the compound of formula (I) has a diameter up to 10 Å, about 5 Å to about 9 Å, or about 6 Å to about 9 Å.

3. The complex of claim 1, wherein the salt comprises an anion selected from the group consisting of PF$_6^-$, halo, sulfate, phosphate, acetate, nitrate, trifluoroacetate, and carbonate.

4. The complex of claim 1, wherein R$^1$ and R$^2$ are the same.

5. The complex of claim 1, wherein R$^1$ and R$^2$ are different.

6. The complex of claim 1, wherein R$^1$ or R$^2$ is methyl, ethyl, propyl, isopropyl, butyl, iso-butyl, sec-butyl, t-butyl, pentyl, hexyl, heptyl, or octyl, or R$^1$ or R$^2$ is phenyl, substituted phenyl, naphthyl, or substituted naphthyl.

7. The complex of claim 6, wherein the phenyl or naphthyl is substituted one or more electron withdrawing group.

8. The complex of claim 6, wherein the phenyl or naphthyl is substituted with one or more electron donating group.

9. The complex of claim 1 in the form of a crystal.

10. The complex of claim 9, wherein the crystal is a single crystalline form.

11. The complex of claim 1, wherein R$^1$ or R$^2$ is further modified with a polymerizable group.

12. A polymer comprising a complex of claim 11.

13. A method of making a complex of claim 1 comprising mixing CBPQT$^{4+}$ and a di-cation of the compound of formula (I) in the presence of a reducing agent to form the complex.

14. The method of claim 13, wherein the reducing agent is zinc dust, an electrochemical reductant, ruthenium(II)tri(2, 2'-bipyridine) (Ru(bpy)$_3^{2+}$), nacent hydrogen, sodium amalgam, NaBH$_4$, sulfite compounds, Zn(Hg) amalgam, oxalic acid, formic acid, ascorbic acid, or a metal having a redox potential of about 0.76V to about 3.04V.

15. A method of making a crystal of claim 9 comprising crystallizing the complex using slow-vapor diffusion or crystallizing the complex in the presence of an externally applied magnetic field.

16. The method of claim 15, wherein the magnetic field controls the direction of crystal growth.

17. The method of claim 16, wherein the magnetic field controls the crystal morphology.

18. The method of claim 17, wherein the crystal morphology is one or more of prism, pyramid, dipyramid, triganoal bipyramid, square pyramid, fiber, and nanowire.

19. The crystal of claim 9, wherein the crystal morphology is one or more of prism, pyramid, dipyramid, triganoal bipyramid, square pyramid, fiber, and nanowire.

20. The crystal of claim 9, wherein the crystal is an electrode.

21. The crystal of claim 20, wherein the electrode is a component in a battery, solar cell, or charge storage device.

* * * * *